(12) United States Patent
Bastianelli et al.

(10) Patent No.: US 11,458,166 B2
(45) Date of Patent: Oct. 4, 2022

(54) FORMULATIONS INVOLVING SOLVENT/DETERGENT-TREATED PLASMA (S/D PLASMA) AND USES THEREOF

(71) Applicants: Bone Therapeutics S.A., Gosselies (BE); Enrico Bastianelli S.P.R.L., Rhode St. Genese (BE)

(72) Inventors: Enrico Bastianelli, Rhode St. Genese (BE); Valentina Albarani, Brussels (BE)

(73) Assignees: Bone Therapeutics S.A, Gosselies (BE); Enrico Bastianelli SPRL, Rhode St. Genèse (BE)

( * ) Notice: Subject to any disclaimer, the term of this patent is extended or adjusted under 35 U.S.C. 154(b) by 0 days.

(21) Appl. No.: 14/431,720

(22) PCT Filed: Sep. 26, 2013

(86) PCT No.: PCT/EP2013/070085
§ 371 (c)(1),
(2) Date: Mar. 26, 2015

(87) PCT Pub. No.: WO2014/049063
PCT Pub. Date: Apr. 3, 2014

(65) Prior Publication Data
US 2015/0238528 A1 Aug. 27, 2015

(30) Foreign Application Priority Data
Sep. 26, 2012 (EP) .................................. 12186027

(51) Int. Cl.
| | | |
|---|---|---|
| *A61K 38/18* | (2006.01) | |
| *A61K 35/16* | (2015.01) | |
| *A61K 31/728* | (2006.01) | |
| *A61K 45/06* | (2006.01) | |
| *A61K 35/28* | (2015.01) | |
| *A61K 35/32* | (2015.01) | |
| *A61K 31/726* | (2006.01) | |
| *C08L 5/08* | (2006.01) | |
| *C08L 5/00* | (2006.01) | |
| *A61K 31/4168* | (2006.01) | |
| *A61K 38/20* | (2006.01) | |
| *A61K 38/29* | (2006.01) | |
| *A61K 47/46* | (2006.01) | |

(52) U.S. Cl.
CPC .......... *A61K 35/16* (2013.01); *A61K 31/4168* (2013.01); *A61K 31/726* (2013.01); *A61K 31/728* (2013.01); *A61K 35/28* (2013.01); *A61K 35/32* (2013.01); *A61K 38/18* (2013.01); *A61K 38/1825* (2013.01); *A61K 38/1841* (2013.01); *A61K 38/1858* (2013.01); *A61K 38/1875* (2013.01); *A61K 38/2053* (2013.01); *A61K 38/29* (2013.01); *A61K 45/06* (2013.01); *A61K 47/46* (2013.01); *C08L 5/00* (2013.01); *C08L 5/08* (2013.01); *A61K 2300/00* (2013.01)

(58) Field of Classification Search
CPC ...... A61K 38/18; A61K 35/16; A61K 31/728; A61K 45/06
See application file for complete search history.

(56) References Cited

U.S. PATENT DOCUMENTS

| | | | |
|---|---|---|---|
| 4,764,369 A | 8/1988 | Neurath | |
| 5,486,359 A | 1/1996 | Caplan et al. | |
| 5,736,396 A | 4/1998 | Bruder et al. | |
| 5,811,094 A | 9/1998 | Caplan et al. | |
| 5,827,740 A | 10/1998 | Pittenger | |
| 5,837,539 A | 11/1998 | Caplan et al. | |
| 5,972,703 A | 10/1999 | Long et al. | |
| 7,662,411 B2 * | 2/2010 | Viswanathan | A61K 35/16 424/530 |
| 2002/0018777 A1 | 2/2002 | Prince | |
| 2004/0082540 A1 * | 4/2004 | Hermida Ochoa | A61K 9/0024 514/54 |
| 2006/0029578 A1 * | 2/2006 | Hoemann | A61K 31/727 424/93.7 |
| 2009/0264477 A1 * | 10/2009 | Zanella | A61K 9/0024 514/351 |
| 2012/0156306 A1 * | 6/2012 | Weissman | A61K 38/18 424/532 |
| 2012/0171169 A1 * | 7/2012 | Pak | A61K 9/0019 424/93.7 |
| 2012/0171182 A1 | 7/2012 | Pak | |

FOREIGN PATENT DOCUMENTS

| | | |
|---|---|---|
| EP | 0322786 A2 | 7/1989 |
| JP | 2003-511468 A | 3/2003 |
| JP | 2008-505065 A | 2/2008 |
| JP | 2010-057942 A | 3/2010 |
| JP | 2010-535188 A | 11/2010 |
| JP | 2011229508 | 11/2011 |

(Continued)

OTHER PUBLICATIONS

Horowitz et al., Blood, 1992, vol. 79(3):826-831.*
Grobler et al., Can. J. Anesth./J. Can. Anesth., 2010, vol. 57:458-467.*
Zhang et al., in Handbook of Glycomics, edited by R.D. Cummings and J.M. Pierce, 2009, Chapter 3, pp. 59-80.*
Benjamin et al: "Plasma components: properties, differences, and uses", 2012, Transfusion, 52:9S-19S.
Horowitz Bet al: "Solvent/Detergent-Treated Plasma: A Virus-Inactivated Substitute for Fresh Frozen Plasma", 1992, Blood, 79:826-831.

(Continued)

*Primary Examiner* — Xiaozhen Xie
(74) *Attorney, Agent, or Firm* — McDonnell Boehnen Hulbert & Berghoff LLP

(57) ABSTRACT

The invention concerns pharmaceutical formulations comprising solvent/detergent (S/D)-treated plasma and a glycosaminoglycan such as hyaluronic acid, and their use for treating diseases, particularly musculoskeletal diseases.

15 Claims, 2 Drawing Sheets

(56) References Cited

FOREIGN PATENT DOCUMENTS

| WO | WO2000/07639 | | 2/2000 | |
|---|---|---|---|---|
| WO | 2009016451 | A2 | 2/2009 | |
| WO | WO-2009016451 | A2 * | 2/2009 | ........... A61K 31/728 |

OTHER PUBLICATIONS

Larking et al: "Total glycosaminoglycans in the plasma of adults: Effects of age and gender, and relationship to plasma lipids: A preliminary study", 1989, Biochemical Medicine and Metabolic Biology, 42:192-197.

Park et al: "Potential of Fortified Fibrin/Hyaluronic Acid Composite Gel as a Cell Delivery Vehicle for Chondrocytes", 2009, Artificial Organs, 33:439-447.

Svae et al: "Quality differences between solvent/detergent plasmas and fresh-frozen plasma", 2007, Transfusion Medicine, 17:318-320.

Theusinger et al: "Relative concentrations of haemostatic factors and cytokines in solvent/detergent-treated and fresh-frozen plasma", 2011, British Journal of Anaesthesia, 106:505-511.

Toyoda et al: "Microdetermination of hyaluronan in human plasma by high-performance liquid chromatography with a graphitized carbon column and postcolumn fluorometric detection", 2011, Journal of Chromatography B: Biomedical Sciences & Applications, 879:950-954.

Meena et al., "Hyaluronic Acid and Derivatives for Tissue Engineering," 2011, J Biotechnol Biomaterial, 1:S3.

Serban et al., "Synthesis, Characterization and Chondroprotective Properties of a Hyaluronan Thioethyl Ether Derivative," 2008, Biomaterials, 29:1388-1399.

Vesna Ivanovic, et al. (2003) "Elevated plasma levels of transforming growth factor-β1 (TGF-β1) in patients with advanced breast cancer: association with disease progression" European Journal of Cancer, 39, pp. 454-461.

Norihide Sato, et al. (2002) "Elevated level of plasma basic fibroblast growth factor in multiple myeloma correlates with increased disease activity" Jpn. J. Cancer Res., 93, pp. 459-466.

Akira Tahara, MD, et al. (1991) "Plasma levels of platelet-derived growth factor in normal subjects and patients with ischemic heart disease" American Heart Journal, vol. 122(4), Part 1, pp. 986-992.

Oates, et al. (2006) "Rheopexy of synovial fluid and protein aggregation", Journal of the Royal Society Interface, vol. 3, pp. 167-174.

Rinaudo, (2008), "Rheological investigation on hyaluronan-fibrinogen interaction", International Journal of Biological Macromolecules, vol. 43, pp. 444-450.

Beeck and Hellstern, 1998, In vitro characterization of solvent/detergent-treated human plasma and of quarantine fresh frozen plasma. Vox Sang. 74, Suppl 1: p. 219-223.

Burgess WH, et al., 1989, The heparin-binding (fibroblast) growth factor family of proteins. Annu. Rev. BioChem., vol. 58, pp. 575-606.

Cole, et al., 2010, Platelet-Rich Plasma. Sports Health, "Platelet-Rich Plasma: Where are we now and where are we going?" vol. 2, pp. 203-210.

Connolly, et al., 1995, Clin. Orthop, "Injectable bone marrow preparations to stimulate osteogenic repair" vol. 313, pp. 8-18.

Cook, et al., 1997, J. Biomed. Mater. Res., "Characterization and development of RGD-peptide-modified poly(lactic acid-co-lysine) as an interactive, resorbable biomaterial" :vol. 35, pp. 513.

Diaz-Romero, et al., 2005, J. Cell Physiol. "Immunophenotypic analysis of human articular chondrocytes: changes in surface markers associated with cell expansion in monolayer culture" vol. 202(3), pp. 731-742.

Doyle, et al., 2003, Coagulation factor content of solvent-detergent plasma compared with fresh frozen plasma. Blood Coagul Fibrinolysis., vol. 14(3), pp. 283-287.

Frescaline, G, et al., 2012, Glycosaminoglycans mimetics potentiate the clonogenicity, proliferation, migration and differentiation properties of rat mesenchymal stem cells. Stem Cell Res., vol. 8(2), pp. 180-192.

Gangji, et al., 2005, Expert Opin Biol Ther, "Stem cell theraphy for osteonecrosis of the femoral head" vol. 5, pp. 437-442.

Gobbi, et al., 2009, Biological approaches for cartilage repair. J. Knee Surg, vol. 22, pp. 36-44.

Gregory, et al., 2004, Analytical Biochemistry, "An Alizarin red-based assay of mineralization by adherent cells in culture: comparison with cetylpyridinium chloride extraction" vol. 329, pp. 77-84.

Grimaud, et al. 2002, et al., recent adcances in TGF-beta effects on chondrocyte metabolism. Potential therapeutic roles of TGF-beta in cartilage disorders. Cytokine Growth Factor Rev. 13, pp. 241-257.

Hausser, H.J., et al., 2004, Low doses and high doses of heparin have different effects on osteoblast-like Soas-2 cells in vitro., J. Cell. Biochem., vol. 91(5), pp. 1062-1073.

Hellstern, P., et al., 2011, The use of solvent/detergent treatment in pathogen reduction of plasma. Transfus. Med. Hemother., vol. 38(1), pp. 65-70.

Hu et al., 1997,Curr Opin Biotechnol, "Large-scale mammalian cell culture", vol. 8, 148.

Jaiswal, et al., 1997, J. Cell Biochem, Osteogenic differentiation of purified, culture-expanded human mesenchymal stem cells in vitro, vol. 64, pp. 295-312.

K. Kitano, 1991, Biotechnology, "Serum-Free Media", vol. 17, 73.

Lyon, M, et al., 1997, The interaction of the transforming growth factor-betas with heparin/heparin sulfate is isoform-specific., J. Biol. Chem., vol. 272(29), pp. 18000-18006.

Mast, et al., 1999, Solvent/detergent-treated plasma has decreased antitrypsin activity and absent antiplasmin activity, vol. 94(11), pp. 3922-3927.

McCaffrey, TA, et al., 1989, Transforming growth factor-beta activity is potentiated by heparin via dissociation of the transforming growth factor beta/alpha 2-macroglobulin inactive complex., vol. 109(1): pp. 441-448.

Mikos, et al., 1993, Biomaterials "Laminated three-dimensional biodegradable foams for use in tissue engineering" vol. 14, pp. 323.

Mikos, et al, 1994, Polymer, "Preparation and characterization of poly(L-lactic acid) foams" vol. 35, pp. 1068.

Pittenger, et al., 1999, Science, "Multilineage potential of adult human mesenchymal stem cells", vol. 284, pp. 143-147.

Sachs, et al., 2005, White blood cell-reactive antibodies are undetectable in solvent/detergent plasma., Transfusion, vol. 45(10), pp. 1628-1631.

Spier, R. 1991, Curr Opin Biotechnol, "Large-Scale Mammalian cell culture: methods, applications and products", vol. 2, 375.

Lubkowska et al., "Growth Factor Content in PRP and their Applicability in Medicine", Apr. 2012, vol. 26 (2) S, 0-0 (J. Biol Reg) 21 pages.

Taniguchi et al., 2019, "Growth factor levels in leukocyte-poor platelet-rich plasma and correlations with donor age, gender, and platelets in the Japanese population", (2019), vol. 6 (4), (Journal of Experimental Orthopaedics), pp. 1-8.

* cited by examiner

A

B

FORMULATIONS INVOLVING SOLVENT/DETERGENT-TREATED PLASMA (S/D PLASMA) AND USES THEREOF

This application is a U.S. national phase application of International Patent Application No. PCT/EP2013/070085 filed on Sep. 26, 2013, which claims the benefit of European patent application 12186027.4, filed Sep. 26, 2012.

FIELD

The invention concerns pharmaceutical formulations and their use for treating diseases such as musculoskeletal diseases, and more particularly bone or joint diseases.

BACKGROUND

Musculoskeletal diseases or disorders can affect the bones, muscles, joints, cartilage, tendons, ligaments, and other connective tissues that support and bind tissues and organs together. These diseases can develop over time or can result for instance by excessive use of the musculoskeletal system or from trauma. Musculoskeletal diseases can be difficult to diagnose and/or treat due to the close relation of the musculoskeletal system to other internal systems.

A possible and promising approach for the treatment of musculoskeletal diseases and in particular of bone diseases and joint diseases is transplantation of mesenchymal stem cells (MSC) capable of undergoing osteogenic or chondrogenic differentiation or of cells that are committed towards osteoblastic or chondroblastic lineage.

MSC have been used previously to treat bone disorders (Gangji et al. Expert Opin Biol Ther, 2005, vol. 5, 437-42). However, although such relatively undifferentiated stem cells can be transplanted, they are not committed to the osteoblastic or chondroblastic lineage and therefore a considerable proportion of so-transplanted stem cells may not eventually contribute to the formation of the desired tissue. Moreover, the quantity of such stem cells obtainable from any possible source tissues is frequently unsatisfactory.

Local delivery of pharmaceutical active ingredients, and in particular localised intra- or peri-osseous or intra- or peri-articular administration of such, is of great interest in musculoskeletal diseases, aiding to increase the local concentration and effectiveness of the ingredients and avoid potential systemic side effects. For example, intra-articular injection of hyaluronic acid (HA) of high molecular weight was effective for restoring the mechanical integrity of joints affected by osteoarthritis. However, HA of high molecular weight has the disadvantage of not providing a completely satisfactory scaffold due to gelification. In another example, bone marrow implantation into the osteonecrotic zone demonstrated beneficial effects in patients suffering from aseptic non-traumatic osteonecrosis of the femoral head (Gangji et al. 2005, supra).

There thus exists a continuous need for further and/or improved pharmaceutical formulations configured for localised administration, such as for intra-osseous, peri-osseous, intra-articular or peri-articular administration, or for intra-tendon, peri-tendon, intra-ligament or peri-ligament administration. Particularly useful formulations may display or attain gel consistency upon administration, whereby pharmaceutical active ingredients included in the formulations are retained in the gel in situ and are gradually released from the gel, i.e., sustained or slow release. Also, where the formulations contain therapeutic cells, gel consistency may provide cell-supportive environment and may ensure proximity of the cells and optional beneficial substances, such as growth factors that stimulate survival, proliferation (propagation) and/or differentiation of the cells.

Fresh frozen plasma (FFP) is prepared in blood banks worldwide mainly as a by-product of red blood cell concentrate preparation. With view of improving safety of FFP, solvent/detergent (S/D) treatment of plasma has been developed in the course of 1980's, resulting in a manufactured product in 1992. S/D treatment and S/D-treated plasma are described inter alia in Horowitz et al. 1992; U.S. Pat. No. 4,764,369; EP 0 322 786; and US 2002/018777. S/D treatment of plasma disrupts the membranes of lipid-enveloped viruses, cells and most protozoa, while leaving the labile coagulation factors intact. The treatment has variable efficacy against bacteria and is substantially ineffective against non-lipid-enveloped viruses. Compared to FFP, S/D-treated plasma displays extremely high safety with respect to transfusion related acute lung injury (TRALI), significantly lower likelihood of provoking allergic reactions, and low batch to batch variation in plasma level coagulation factors. JP2011229508 (abstract) concerns a cell composition comprising skeleton myoblasts embedded in gel including plasma.

WO 2009/016451 concerns the use of a homologous or autologous blood derived substance alone or in combination with hyaluronic acid to treat an articular disease, articular pain or skin. Park et al. 2009 concerns the combination of fibrin and hyaluronic acid as a cell delivery vehicle for rabbit chondrocytes with applications in cartilage repair.

SUMMARY

The present inventors have found pharmaceutical formulations addressing one or more of the above-mentioned problems in the art.

An aspect of the invention relates to a pharmaceutical formulation comprising solvent/detergent-treated plasma (S/D plasma) and a glycosaminoglycan.

As evidenced in the Examples section, formulations applying the principles of the present invention have the advantageous property to gelify in vitro in contact with body fluids of subjects, such as human subjects, especially serum or synovial fluids, for example from patients suffering from knee osteoarthritis or bone diseases. Such formulations applying the principles of the present invention are shown to gelify in vitro in contact with body fluids such as whole blood, and hence to have the property to gelify in situ (in situ coagulation) when contacted with body fluids such as whole blood. For example, the present formulation may advantageously provide a natural environment of autologous growth factors from the whole blood. The formulations display particularly good gel-forming behaviour in situ (i.e., when administered at a given place or site (e.g., bone, joint, tendon or ligament) of a subject's body), producing advantageously viscous formulations. For instance, once injected in articular defects, the present formulations allow gelification in situ and restore the physiological and rheological states of an arthritic joint such as an arthritic knee joint. Further, this viscous quality can ensure localised delivery and/or sustained release of components of the formulations, namely of the S/D plasma, which can comprise beneficial biological substances such as endogenous growth factors, and/or of the glycosaminoglycan. The viscous quality can also allow to incorporate additional pharmaceutical active ingredient(s) (such as, without limitation, a cell composition, a pharmaceutical active compound, a protein, a peptide, and/or a small organic molecule) into the formulations, and thereby achieve localised delivery and/or sustained release of such ingredient(s). The inventors also envisage that the viscous quality may protect the components of the formulations and/or additional pharmaceutical active ingredient(s) included therein from the physical environment, thereby improving the overall stability (e.g., stability against enzymatic degradation) of the components and ingredients in vivo. The inventors further postulate that the viscous quality may allow to improve articular function by an extended lubricating action on the joint, thereby better restoring the mechanical integrity of the joint. The inventors also envisage that the formulations may allow to improve bone healing by an osteoinductive action.

The pharmaceutical formulation may typically comprise one or more pharmaceutically acceptable excipients (e.g., solvents, carriers, diluents, etc.), particularly excipients compatible with the intended mode of administration of the formulation, such as in particular parenteral and preferably intra-osseous, peri-osseous, intra-articular, or peri-articular administration of the formulation, or for intra-tendon, peri-tendon, intra-ligament or peri-ligament administration of the formulation.

The pharmaceutical formulation may be produced by a method comprising combining (e.g., admixing or including in a kit of parts) the S/D plasma and the glycosaminoglycan; such methods are encompassed herein. Hence, the glycosaminoglycan may be suitably denoted as exogenous, or exogenously added to the S/D plasma, or as provided in addition to the S/D plasma.

The pharmaceutical formulation may be configured for separate, simultaneous or sequential in any order administration of the S/D plasma and the glycosaminoglycan and, when included, the additional pharmaceutical active ingredient(s). Accordingly, the pharmaceutical formulation may be an admixture of all of its individual constituents, or it may be a combination, such as a kit of parts, comprising the individual constituents separately or comprising admixture(s) of two or more but not all of the individual constituents. Hence, the formulation may be constituted as a kit of parts comprising S/D plasma and a glycosaminoglycan.

The pharmaceutical formulation may be provided in a medical device. Such medical device advantageously allows for parenteral administration, such as intra-osseous, peri-osseous, intra-articular, or peri-articular administration, or for intra-tendon, peri-tendon, intra-ligament or peri-ligament administration, of the formulation to a subject in need thereof.

Preferably, the S/D plasma may be human S/D plasma, such that pharmaceutical formulations comprising human S/D plasma are particularly suited for administration to human subjects.

In certain embodiments, the glycosaminoglycan may be selected from the group consisting of hyaluronic acid and derivatives thereof, a proteoglycan and derivatives thereof, a chondroitin sulfate, a keratan sulfate, a chitosan and derivatives thereof, a chitin and derivatives thereof. The formulation may comprise one or more glycosaminoglycans. The formulation may thus comprise one glycosaminoglycan or a mixture of glycosaminoglycans selected from the group consisting of hyaluronic acid and derivatives thereof, a proteoglycan and derivatives thereof, a chondroitin sulfate, a keratan sulfate, a chitosan and derivatives thereof, a chitin and derivatives thereof.

Without limitation, the pharmaceutical formulation can comprise the glycosaminoglycan in a concentration ranging from about 0.10 mg/ml to about 200 mg/ml, preferably from about 1.0 mg/ml to about 100 mg/ml, more preferably from about 2.0 mg/ml to about 50 mg/ml, e.g., about 10 mg/ml, about 20 mg/ml, about 30 mg/ml or about 40 mg/ml.

Typically, an intra- or peri-osseous injection or an intra- or peri-articular injection may have a volume of between about 2 ml and about 4 ml.

Where the glycosaminoglycan displays therapeutic benefit of its own, it may be included in a therapeutically effective amount, such as the exemplary amounts recited in this paragraph.

In particularly preferred embodiments, the glycosaminoglycan may be hyaluronic acid or a derivative thereof.

Without limitation, suitable derivatives may be salts of hyaluronic acid, such as preferably sodium hyaluronate. The hyaluronic acid or derivative thereof can have a low (<900 kDa) or high (>900 kDa) molecular mass. Particularly preferred may be hyaluronic acid or derivatives thereof with high (>900 kDa) molecular mass. For instance, the hyaluronic acid or derivative thereof may have a molecular mass ranging from about $1 \times 10^6$ Da to about $6 \times 10^6$ Da or more, such as ranging from about $1 \times 10^6$ Da to about $4 \times 10^6$ Da, such as ranging from about $1.3 \times 10^6$ Da to about $3 \times 10^6$ Da.

Without limitation, the pharmaceutical formulation can comprise the hyaluronic acid or derivative thereof in a concentration ranging from about 0.10 mg/ml to about 200 mg/ml, preferably from about 1.0 mg/ml to about 100 mg/ml, more preferably from about 2.0 mg/ml to about 50 mg/ml.

In certain embodiments, the pharmaceutical formulation may comprise one or more other ingredients in addition to the S/D plasma and glycosaminoglycan. In other embodiments, the S/D plasma and glycosaminoglycan may be the only components of the formulation; hence, in such embodiments the pharmaceutical formulation may consist of or consist essentially of the S/D plasma and glycosaminoglycan. In yet further embodiments, the pharmaceutical formulation may comprise one or more other ingredients in addition to the S/D plasma and glycosaminoglycan, but such additional ingredients are not pharmaceutical active ingredients.

In certain embodiments, the pharmaceutical formulation may advantageously further comprise one or more pharmaceutical active ingredients.

The applicability of the present invention is not limited to any pharmaceutical active ingredient or class of pharmaceutical active ingredients. The pharmaceutical active ingredient may be pharmacologically active itself, or may be converted into a pharmacologically active species by a chemical or enzymatic process in the body, i.e., the pharmaceutical active ingredient may be a prodrug. The present pharmaceutical formulations may be particularly useful for poorly-stable pharmaceutical active ingredients. Illustrative non-limiting examples of poorly-stable pharmaceutical active ingredients include peptides and proteins such as growth factors, peptide-like active ingredients, antibodies and vaccines, small interfering RNA (siRNA), DNA, hormones, etc.

The term "pharmaceutical active ingredient" also encompasses any pharmacologically active salts, esters, N-oxides or prodrugs of the title compound or substance.

Moreover, combination of two or more pharmaceutical active ingredients or doses combinations may be included as the drug component. In this case, the release of each active ingredient may be identical or different such as for instance in case of a combination of two active ingredients in which the first one is presented as an immediate release form and the second one as a controlled release. Similarly, a combination of immediate release and controlled release form may also be obtained for the same active ingredient, in order to provide a rapid and sustained effect.

In certain embodiments, the pharmaceutical formulation may further comprise serum. The addition of serum to the present formulation may allow to a certain extent to improve the gelification of the formulation.

For example, the serum may be allogeneic or autologous with respect to the subject receiving the formulation. Preferably, the serum may be human serum, such that pharmaceutical formulations further comprising human serum are particularly suited for administration to human subjects. For example, the formulation may contain serum and S/D plasma such that the value calculated as (volume of serum in the formulation)/(volume of serum in the formulation+ volume of S/D plasma in the formulation) is between about 0.01 and about 0.40, preferably between about 0.05 and about 0.15, more preferably about 0.10.

In certain embodiments, the pharmaceutical formulation may further comprise whole blood or a fractionated component of whole blood. The addition of whole blood or said fractionated component, preferably of whole blood, to the present formulation may allow at least partially to improve the gelification of the formulation.

The present formulations comprising whole blood or said fractionated component thereof advantageously comprise platelet-derived growth factors useful in regenerative medicine, in particular for stimulating repair of bone, cartilage, tendon or ligaments defects or for replacing damaged bones, cartilages, tendons or ligaments (Gobbi et al., 2009; Grimaud et al., 2002; Cole et al., 2010).

For example, the whole blood may be allogeneic or autologous with respect to the subject receiving the formulation. Preferably, the whole blood may be human whole blood, such that pharmaceutical formulations further comprising human whole blood are particularly suited for administration to human subjects. For example, the formulation may contain whole blood and S/D plasma such that the value calculated as (volume of whole blood in the formulation)/(volume of whole blood in the formulation+ volume of S/D plasma in the formulation) is between about 0.01 and about 0.40, preferably between about 0.05 and about 0.15, more preferably about 0.10.

In preferred embodiments, the one or more pharmaceutical active ingredient is, each independently, selected from the group consisting of: a cell composition, a pharmaceutical active compound, a protein, a peptide, and a small organic molecule.

Preferably, the cell composition may comprise mesenchymal stem cells (MSC), osteoprogenitors, osteoblastic cells, osteocytes, chondroblastic cells, and/or chondrocytes. The pharmaceutical formulation thus allows for delivery of such cell composition. This viscous quality of the present pharmaceutical formulations can ensure localised delivery of and suitable supportive environment for the delivered cells.

Particularly preferably, the cells of the cell composition may be animal cells, preferably warm-blooded animal cells, more preferably mammalian cells, such as human cells or non-human mammalian cells, and most preferably human cells.

In further embodiments, the pharmaceutical active compound may be an anti-inflammatory substance. In preferred embodiments, the pharmaceutical active compound may be an alpha-2 adrenergic receptor agonist. Preferably, the alpha-2 adrenergic receptor agonist may be selected from the group consisting of clonidine and derivatives thereof.

In certain embodiments, the alpha-2 adrenergic receptor agonist may be selected from the group consisting of clonidine and derivatives thereof, including 2,6-dimethylclonidine, 4-azidoclonidine, 4-carboxyclonidine-methyl 3,5-dichlorotyrosine, 4-hydroxyclonidine, 4-iodoclonidine, alinidine, apraclonidine, chlorethylclonidine, clonidine 4-isothiocyanate, clonidine 4-methylisothiocyanate, clonidine receptor, clonidine-displacing substance, hydroxyphenacetyl aminoclonidine, N,N'-dimethylclonidine, p-aminoclonidine, and tiamenidine; imidazolidines, including imidazolines, impromidine, detomidine, medetomidine, dexmedetomidine, levamisole, losartane, lofexidine, miconazole, naphazoline, niridazole, nitroimidazoles, ondansetron, oxymetazoline, phentolamine, tetramisole, thiamazole, tizanidine, tolazoline, trimetaphan; imidazoles, including 4-(3-butoxy-4-methoxybenzyl) imidazolidin-2-one, urocanic acid, amino-imidazole carboxamide, antazoline, biotine, bis(4-methyl-1-homo piperazinylthiocarbonyl) disulfide, carbimazole, cimetidine, clotrimazole, creatinine, dacarbazine, dexmedetomidine, econazole, enoximone, ethymizol, etomidate, fadrozole, fluspirilene, idazoxan, mivazerol; guanidines, including agmatine, betanidine, biguanides, cimetidine, creatine, gabexate, guanethidine, guanethidine sulfate, guanclofine, guanfacine, guanidine, guanoxabenz, impromidine, iodo-3 benzylguanidine, methylguanidine, mitoguazone, nitrosoguanidines, pinacidil, robenidine, sulfaguanidine, zanamivir; alpha-methyinorepherine, azepexole, 5-bromo-6-(2 imidazolidine-2-ylamino) quinoxalin, formoterol fumarate, indoramin, 6-allyl-2-amino-5,6,7,8-tetrahydro4H-thiazolo[4,5-d]azepine diHCl, nicergoline, rilmenidine, and xylazine.

In certain embodiments, the pharmaceutical formulation may further comprise one or more substance with osteogenic, osteo-inductive and/or osteo-conductive properties. In preferred embodiments, such substance may be selected from the group comprising or consisting of a fibroblast growth factor (FGF), preferably FGF-2, a transforming growth factor beta (TGFB), preferably TGFB-1, platelet-derived growth factor (PDGF), interleukin-8 (IL-8), a bone morphogenetic protein (BMP), for example any one or more of BMP-2, BMP-4, BMP-6 and BMP-7, parathyroid hormone (PTH), parathyroid hormone-related protein (PTHrp), and stem cell factor (SCF).

Hence, in certain embodiments, the pharmaceutical active protein or peptide may be a growth factor, preferably a growth factor selected from the group consisting of a FGF, a TGFB, PDGF, IL-8, a BMP, PTH, PTHrp, and SCF, more preferably a growth factor selected from the group consisting of FGF-2, TGFB-1, PDGF, IL-8, BMP-2, BMP-4, BMP-6, BMP-7, PTH, PTHrp, and SCF.

Preferably, the pharmaceutical formulation may be configured for parenteral administration, such as parenteral injection, more preferably for intra-osseous, peri-osseous, intra-articular or peri-articular administration, such as intra-osseous, peri-osseous, intra-articular or peri-articular injection, or for intra-tendon, peri-tendon, intra-ligament or peri-ligament administration, such as, intra-tendon, peri-tendon, intra-ligament or peri-ligament injection.

A related aspect concerns the pharmaceutical formulation as described above for use in the treatment (including throughout the present specification therapeutic and/or preventative measures) of a musculoskeletal disease. Preferably, said musculoskeletal disease may be a bone disease or a joint disease. Alternatively or in addition, said musculoskeletal disease may affect tendons and/or ligaments.

Also intended is the use of the pharmaceutical formulation as described above for the manufacture of a medicament for the treatment of a musculoskeletal disease, preferably a bone disease or a joint disease. Alternatively or in addition, said musculoskeletal disease may affect tendons and/or ligaments.

Further intended is a method for treating a musculoskeletal disease, preferably a bone disease or a joint disease (alternatively or in addition, said disease may affect tendons and/or ligaments), in a subject in need of such treatment, comprising administering to said subject a therapeutically or prophylactically effective amount of the pharmaceutical formulation as described above.

Expanding on these findings, the present inventors have realised the use of the aforementioned formulations as a pharmaceutical excipient, more preferably as a sustained release or slow release pharmaceutical excipient. Accordingly, a related aspect provides the use of a formulation comprising S/D plasma and a glycosaminoglycan as a pharmaceutical excipient, preferably as a pharmaceutical excipient in a pharmaceutical formulation configured for parenteral administration, more preferably for intra-osseous, peri-osseous, intra-articular, or peri-articular administration, or for intra-tendon, peri-tendon, intra-ligament or peri-ligament administration.

Also disclosed is thus a formulation comprising S/D plasma and a glycosaminoglycan for use as a pharmaceutical excipient, more preferably for use as a sustained release or slow release pharmaceutical excipient, preferably for use as a pharmaceutical excipient for the treatment of a musculoskeletal disease, preferably a bone disease or a joint disease (alternatively or in addition, said disease may affect tendons and/or ligaments). Further disclosed is the use of a formulation comprising S/D plasma and a glycosaminoglycan for the manufacture of a pharmaceutical excipient, more preferably a sustained release or slow release pharmaceutical excipient, preferably for the manufacture of a pharmaceutical excipient for the treatment of a musculoskeletal disease, preferably a bone disease or a joint disease (alternatively or in addition, said disease may affect tendons and/or ligaments). Still further provided is a method for treating a musculoskeletal disease, preferably a bone disease or a joint disease (alternatively or in addition, said disease may affect tendons and/or ligaments) in a subject in need of such treatment, comprising administering to said subject a formulation comprising S/D plasma and a glycosaminoglycan as a pharmaceutical excipient, more preferably as a sustained release or slow release pharmaceutical excipient.

Preferably, the S/D plasma may be human S/D plasma, such that pharmaceutical formulations comprising human S/D plasma are particularly suited for administration to human subjects.

Also disclosed herein is the use of S/D plasma as a pharmaceutical excipient, preferably as a pharmaceutical excipient in a pharmaceutical formulation configured for parenteral administration, more preferably for intra-osseous, peri-osseous, intra-articular, or peri-articular administration, or for intra-tendon, peri-tendon, intra-ligament or peri-ligament administration.

Further disclosed is thus S/D plasma for use as a pharmaceutical excipient, more preferably for use as a sustained release or slow release pharmaceutical excipient, preferably for use as a pharmaceutical excipient for the treatment of a musculoskeletal disease, preferably a bone disease or a joint disease (alternatively or in addition, said disease may affect tendons and/or ligaments). Further disclosed herein is the use of S/D plasma for the manufacture of a pharmaceutical excipient, more preferably a sustained release or slow release pharmaceutical excipient, preferably for the manufacture of a pharmaceutical excipient for the treatment of a musculoskeletal disease, preferably a bone disease or a joint disease (alternatively or in addition, said disease may affect tendons and/or ligaments). Still further provided is a method for treating a musculoskeletal disease, preferably a bone disease or a joint disease (alternatively or in addition, said disease may affect tendons and/or ligaments) in a subject in need of such treatment, comprising administering to said subject S/D plasma as a pharmaceutical excipient, more preferably as a sustained release or slow release pharmaceutical excipient.

Preferably, the S/D plasma may be human S/D plasma, such that pharmaceutical formulations comprising human S/D plasma are particularly suited for administration to human subjects.

Also disclosed herein is the use of the aforementioned formulations as a cell culture medium supplement. Accordingly, a related aspect provides the use of a formulation comprising S/D plasma and a glycosaminoglycan as a cell culture medium supplement. Such formulations may advantageously allow obtaining cells or cell cultures with improved properties.

Throughout this aspect of the invention and any of its embodiments, the S/D plasma may preferably be mammalian S/D plasma, more preferably human S/D plasma. Also throughout this aspect of the invention and any of its embodiments, the serum may be mammalian serum, more preferably human serum. Also preferably, the S/D plasma may be mammalian S/D plasma and the serum may be mammalian serum, or the S/D plasma may be human S/D plasma and the serum may be human serum. Human plasma and/or serum may be particularly advantageous for administration to human subjects. Also throughout this aspect of the invention and any of its embodiments, the whole blood may be mammalian whole blood, more preferably human whole blood. Also preferably, the S/D plasma may be mammalian S/D plasma and the whole blood may be mammalian whole blood, or the S/D plasma may be human S/D plasma and the whole blood may be human whole blood. Human plasma and/or whole blood may be particularly advantageous for administration to human subjects.

Also disclosed herein are pharmaceutical formulations as taught above, and the corresponding uses thereof, wherein the glycosaminoglycan is omitted from the formulations. Hence, such formulations may in particular comprise S/D plasma (preferably human S/D plasma) and any one or more components as taught above, in particular, and any one or more of: the serum, the whole blood or the fractionated component thereof, the one or more pharmaceutical active ingredients (such as, each independently, selected from the group consisting of the cell composition, the pharmaceutical active compound, the protein, the peptide, and the small organic molecule. Such formulations may also display satisfactory gel-forming behaviour.

The above and further aspects and preferred embodiments of the invention are described in the following sections and in the appended claims. The subject-matter of appended claims is hereby specifically incorporated in this specification.

Bone repair can be clearly seen (mineralized areas) in the treated mice (B) compared to control without IL-8 (A).

Figure 1:
FIG. 1 illustrates X-ray view of bone tissue repair/formation 4 weeks after the administration of a formulation containing S/D plasma, IL-8 and $CaCl_2$ to a bone defect site in a immunocompetent mouse model of calvaria osteotomy.
Figure 1:
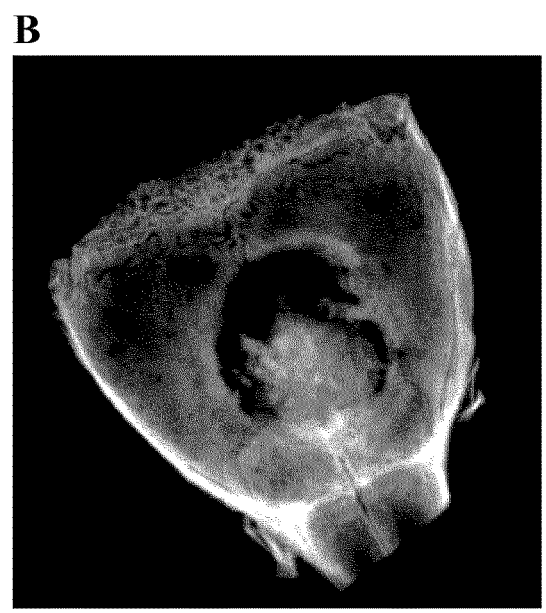
Figure 2:
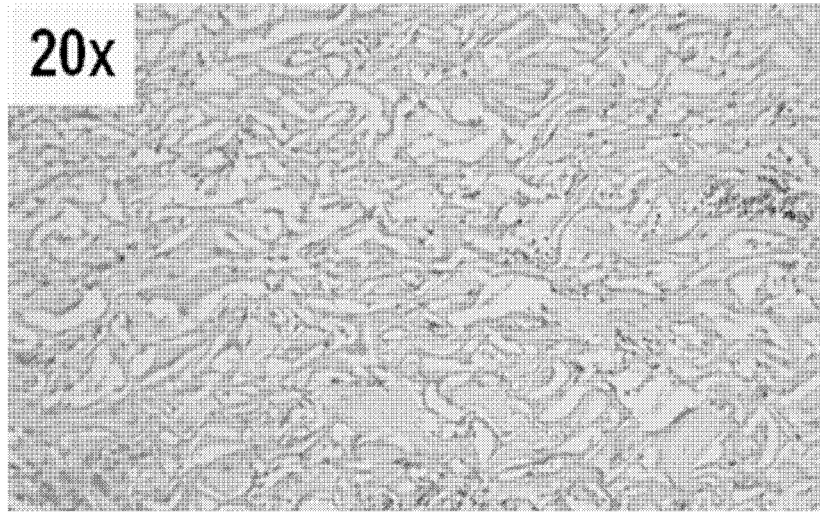
Figure 2:
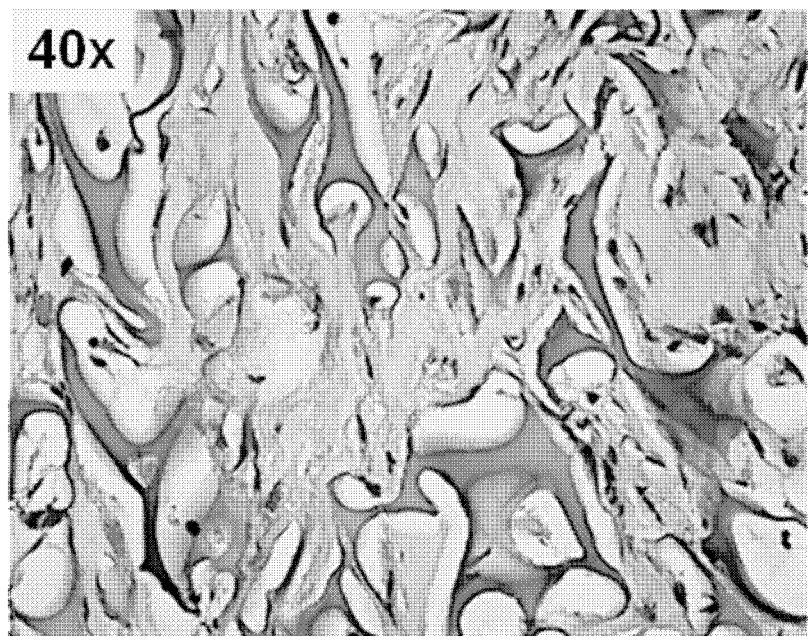

FIG. 2 provides microscopic analysis of the newly formed tissue shown in FIG. 1B, at 20 times (A) and 40 times (B) magnification. Four weeks after the administration of a formulation containing S/D plasma, IL-8 and $CaCl_2$ to a bone defect site in a immunocompetent mouse model of calvaria osteotomy, the empty collagen matrix presents broad areas of mineralized and non-mineralized osteoid and a large number of vessels.

DESCRIPTION OF EMBODIMENTS

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

General techniques in cell culture and media uses are outlined inter alia in Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991).

The terms "pharmaceutical formulation", "pharmaceutical composition", or "pharmaceutical preparation" may be used interchangeably herein. Likewise, the terms "formulation", "composition", or "preparation" may be used interchangeably herein.

The term "plasma" is as conventionally defined. Plasma is usually obtained from a sample of whole blood, provided or contacted with an anticoagulant, (e.g., heparin, citrate, oxalate or EDTA). Subsequently, cellular components of the blood sample are separated from the liquid component (plasma) by an appropriate technique, typically by centrifugation. The term "plasma" therefore refers to a composition which does not form part of a human or animal body.

The terms "solvent/detergent-treated plasma", "S/D-treated plasma", or "S/D plasma" generally refer to decellularised plasma obtainable or obtained by a method comprising the steps of: (a) treating plasma with a solvent and a detergent and (b) filtering the solvent/detergent-treated plasma.

The plasma to be treated in step (a) may be any plasma as conventionally defined such as fresh plasma, fresh frozen plasma, thawed frozen plasma, or cryoprecipitate, cryosupernatants or concentrates from frozen plasma as well as dilution products thereof. Plasma is usually obtained from a sample of whole blood, or from a sample obtained by apheresis.

Solvents such as di- or trialkylphosphates and detergents are described in U.S. Pat. No. 4,764,369. The solvent used for preparing S/D plasma preferably is a dialkylphosphate or a trialkylphosphate, both having alkyl groups which contain 1 to 10 carbon atoms, especially 2 to 10 carbon atoms. Illustrative examples of solvents may include tri-(n-butyl) phosphate, tri-(t-butyl)phosphate, tri-(n-hexyl)phosphate, tri-(2-ethylhexyl)phosphate, or tri-(n-decyl)phosphate. A preferred solvent is tri-(n-butyl)phosphate. Mixtures of different trialkylphosphates can also be employed as well as phosphates having alkyl groups of different alkyl chains, for example, ethyl, di(n-butyl)phosphate. Similarly, the respective dialkylphosphates can be employed including those of different alkyl group mixtures of dialkylphosphate. Furthermore, mixtures of di- and trialkylphosphates can be employed.

The solvent such as di- or trialkylphosphate for use in the treatment step (a) preferably is employed in an amount ranging from about 0.01 mg/ml to about 100 mg/ml, and preferably from about 0.1 mg/ml to about 10 mg/ml. Stated differently, di- or trialkylphosphates for use in the treatment step (a) preferably are employed in an amount ranging from about 0.001% w/v to about 10% w/v, and preferably from about 0.01% w/v to about 1% w/v.

The detergent used for preparing S/D plasma preferably is a non-toxic detergent. Contemplated nonionic detergents include those which disperse at the prevailing temperature at least 0.1% by weight of the fat in an aqueous solution containing the same when 1 gram detergent per 100 ml of solution is introduced therein. Illustrative examples of detergents may include polyoxyethylene derivatives of fatty acids, partial esters of sorbitol anhydrides, for example, those products known commercially as "Tween 80", "Tween 20" and "polysorbate 80" and nonionic oil soluble water detergents such as that sold commercially under the trademark "Triton X 100" (oxyethylated alkylphenol). Also contemplated is sodium deoxycholate as well as the "Zwittergents" which are synthetic zwitterionic detergents known as "sulfobetaines" such as N-dodecyl-N, N-methyl-2-ammonio-1 ethane sulphonate and its congeners or nonionic detergents such as octyl-beta-D-glucopyranoside.

The amount of detergent may range from about 0.001% v/v to about 10% v/v, preferably from about 0.01% v/v to 1.5% v/v.

The treatment with solvent and detergent preferably is effected at a temperature between −5° C. and 70° C., preferably between 0° C. and 60° C. The time of such treatment (contact) is at least 1 minute, preferably at least 1 hour and generally 4 to 24 hours. The treatment is normally effective at atmospheric pressure, although subatmospheric and superatmospheric pressures may also be employed.

Normally, after the treatment, the solvent such as trialkylphosphate and the detergent are removed. The solvent and detergent may be removed by any technique suitable for separating the solvent and detergent from the plasma. When a nonionic detergent is employed with the solvent such as trialkylphosphate, they may be removed by: (1) diafiltration using microporous membranes such as TEFLON which retain the plasma proteins; (2) absorption of desired plasma components on chromatographic or affinity chromatographic supports; (3) precipitation, for example, by salting out of plasma proteins; (4) lyophilization, etc.

Solvents such as dialkylphosphate or trialkylphosphate may be removed as follows: (a) removal from antihemophilic factor (AHF) can be effected by precipitation of AHF with 2.2 molar glycine and 2.0M sodium chloride (b) removal from fibronectin can be effected by binding the fibronectin on a column of insolubilized gelatin and washing the bound fibronectin free of reagent.

The filtering step (b) is generally performed with a 1 μm filter to remove cells and debris, followed by sterile filtration using a 0.2 μm filter.

By virtue of a preferred example, as described by Horowitz et al., 1992 (Blood, 3, 826-831), S/D plasma mat be prepared as follows: FFP may be rapidly thawed and may be treated with stirring for 4 hours with 1% (v/v) tri-(N-butyl)-phosphate (TNBP) and 1% (v/v) polyoxyethylene-p-t-octylphenol (Triton X-100) at 30° C. After treatment, edible oil such as soybean oil (5% v/v) or castor oil may be added, gently mixed for 30 minutes, and may be removed by centrifugation at 10,000 g for 20 minutes. The clarified plasma may be applied to a column of Waters Prep C18 resin such that the ratio of plasma to column volume is 6 and the contact time may be 3 minutes. The column eluate may be filtered on a 0.2 μm filter.

For example, S/D plasma is commercially available as Octaplas® (Octapharma AG, Lachen, Switzerland).

The term "S/D plasma" encompasses plasma comprising a reduced concentration or activity of Plasmin Inhibitor, such as Plasmin Inhibitor level equal to or less than 0.60 IU/ml or equal to or less than 0.50 IU/ml, for example Plasmin Inhibitor level between 0.20 and 0.30 IU/ml, more specifically between 0.22 and 0.25 IU/ml.

When compared with fresh frozen plasma (FFP), S/D plasma may comprise a reduced amount and/or activity of one or more of plasmin inhibitor, protein S, Factor XI, Factor V, Factor VIII, Factor X, α2 antiplasmin, anti-trypsin, von Willebrand factor (vWF), and von Willebrand factor-cleaving protease (VWFCP) also known as disintegrin and metalloproteinase with a thrombospondin type 1 motif, member 13 (ADAMTS-13), tumor necrosis factor-alpha (TNFα), interleukin-8 (IL-8), interleukin-10 (IL-10) (Benjamin and McLaughlin, 2012, Svae et al., 2007; Beeck and Hellstern, 1998; Doyle et al., 2003; Mast et al., 1999, Theusinger et al., 2011) and/or may comprise an increased amount and/or activity of Factor VII (Doyle et al., 2003).

The S/D plasma may be used directly in the present pharmaceutical formulations. They can also be appropriately stored for later use (e.g., for shorter time periods, e.g., up to about 1-2 weeks, at a temperature above the respective freezing points of plasma or serum, but below ambient temperature, this temperature will usually be about 4° C. to 5° C.; or for longer times by freeze storage, usually at between about −70° C. and about −80° C.).

The S/D plasma may be heat inactivated as known in the art, particularly to remove the complement. Where the present pharmaceutical formulations employ S/D plasma autologous to the subject to be treated, it may be unnecessary to heat inactivate the S/D plasma. Where the S/D plasma is at least partly allogeneic to the subject to be treated, it may be advantageous to heat inactivate the S/D plasma.

The pharmaceutical formulations of the present invention may comprise S/D plasma which is autologous to the subject to be treated. The term "autologous" with reference to S/D plasma denotes that the S/D plasma is obtained from the same subject to be contacted or treated with the S/D plasma. The pharmaceutical formulations of the present invention may comprise S/D plasma which is "homologous" or "allogeneic" to the subject to be treated, i.e., obtained from one or more (pooled) subjects other than the subject to be contacted or treated with the S/D plasma. The pharmaceutical formulations of the present invention may also comprise a mixture of autologous and homologous (allogeneic) S/D plasma as defined above. Preferably, the pharmaceutical formulations may comprise S/D plasma which is "allogeneic" to the subject to be treated. Advantageously, allogeneic S/D plasma is commercially available and hence is an unrestricted source of plasma.

The term "serum" is as conventionally defined. Serum can be usually obtained from a sample of whole blood by first allowing clotting to take place in the sample and subsequently separating the so formed clot and cellular components of the blood sample from the liquid component (serum) by an appropriate technique, typically by centrifugation. Clotting can be facilitated by an inert catalyst, e.g., glass beads or powder. Alternatively, serum can be obtained from plasma by removing the anticoagulant and fibrin. The term "serum" hence refers to a composition which does not form part of a human or animal body.

The serum may be used directly in the pharmaceutical formulations as taught herein. They can also be appropriately stored for later use (e.g., for shorter time periods, e.g., up to about 1-2 weeks, at a temperature above the respective freezing points of plasma or serum, but below ambient temperature, this temperature will usually be about 4° C. to 5° C.; or for longer times by freeze storage, usually at between about −70° C. and about −80° C.).

The serum can be heat inactivated as known in the art, particularly to remove the complement. Where the present pharmaceutical formulations employ serum autologous to the cells cultured in the presence thereof, it may be unnecessary to heat inactivate the serum. Where the serum is at least partly allogeneic to the cultured cells, it may be advantageous to heat inactivate the serum.

Optionally, the serum may also be sterilized prior to storage or use, using conventional microbiological filters, preferably with pore size of 0.2 μm or smaller.

In certain embodiments, the pharmaceutical formulations may employ serum which is autologous to the subject to be treated. The term "autologous" with reference to serum denotes that the serum is obtained from the same subject to be contacted with the serum. In certain embodiments, the pharmaceutical formulations may employ serum which is "homologous" or "allogeneic" to the subject to be treated, i.e., obtained from one or more (pooled) subjects other than the subject to be contacted with the serum. In certain embodiments, the pharmaceutical formulations may employ a mixture of autologous and homologous (allogeneic) sera as defined above.

The term "whole blood" is as conventionally defined. Preferably the sample is readily obtainable by minimally invasive methods, allowing the removal or isolation of the whole blood from the subject. The whole blood is usually provided or contacted with an anticoagulant, (e.g., heparin, citrate, oxalate or EDTA).

The whole blood may be used directly in the pharmaceutical formulations as taught herein. The whole blood can also be appropriately stored for later use (e.g., for shorter time periods, e.g., up to about 1-4 weeks, at a temperature above the freezing point of whole blood, but below ambient temperature, this temperature will usually be about 4° C. to 5° C.; or for longer times by freeze storage, usually at between about −70° C. and about −160° C., such as between about −70° C. and about −80° C., such as at about −160° C.).

In certain embodiments, the pharmaceutical formulations may employ whole blood which is autologous to the subject to be treated. The term "autologous" with reference to whole blood denotes that the whole blood is obtained from the same subject to be contacted with the whole blood. In certain embodiments, the pharmaceutical formulations may employ whole blood which is "homologous" or "allogeneic" to the subject to be treated, i.e., obtained from one or more (pooled) subjects other than the subject to be contacted with the whole blood. In certain embodiments, the pharmaceutical formulations may employ a mixture of autologous and homologous (allogeneic) whole blood as defined above.

In certain embodiments, the glycosaminoglycan may be selected from the group consisting of hyaluronic acid and derivatives thereof, a proteoglycan and derivatives thereof, a chondroitin sulfate, a keratan sulfate, a chitosan and derivatives thereof, a chitin and derivatives thereof.

The terms "hyaluronic acid" or "HA" may be used interchangeably with "hyaluronan" or "hyaluronate". The term "hyaluronic acid" refers to an anionic, non-sulfated polymer of disaccharides composed of D-glucuronic acid and N-acetyl-D-glucosamine, linked via alternating β-1,4 and β-1,3 glycosidic bonds. Hyaluronic acid derivatives include but are not limited to salts of hyaluronate such as sodium hyaluronate or an ester of hyaluronic acid with an alcohol of the aliphatic, heterocyclic or cycloaliphatic series, or a sulphated form of hyaluronic acid or combination of agents comprising hyaluronic acid.

The term "proteoglycan" refers to proteins with one or more covalently attached glycosaminoglycan (GAG) chain(s). The glycosaminoglycan can be a proteoglycan selected from decorin, biglycan, testican, fibromodulin, lumican, versican, perlecan, neurocan or aggrecan.

The term "chondroitin sulfate" refers to a polymer of disaccharides composed of N-acetylgalactosamine and glucuronic acid, each of which can be sulfated in variable positions and quantities. The chondroitic sulfate can be selected from chondroitin-4-sulfate, chondroitin-6-sulfate, chondroitin-2,6-sulfate, chondroitin-4,6-sulfate.

The term "keratan sulfate" may be used interchangeably with "keratosulfate" and refers to a polymer of repeating disaccharides-3Galβ1-4GlcNAcβ1-which can be sulfated at carbon position 6 (C6) of either or both the Gal or GlcNAc monosaccharides.

The term "chitosan" refers to a linear polymer composed of randomly distributed β-(1-4)-linked D-glucosamine (deacetylated unit) and N-acetyl-D-glucosamine (acetylated unit).

The term "chitin" refers to a polymer composed of β-(1,4)-linked N-acetylglucosamine.

In certain embodiments, the pharmaceutical formulation further comprises one or more pharmaceutical active ingredients.

Such pharmaceutical active ingredients may encompass for example cell compositions.

In certain embodiments, the cell composition may comprise mesenchymal stem cells (MSC), osteoprogenitors, osteoblastic cells, osteocytes, chondroblastic cells, and/or chondrocytes.

The term "mesenchymal stem cell" or "MSC", as used herein, refers to an adult, mesoderm-derived stem cell that is capable of generating cells of mesenchymal lineages, typically of two or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. MSC may be isolated from, e.g., bone marrow, trabecular bone, blood, umbilical cord, placenta, foetal yolk sac, skin (dermis), specifically foetal and adolescent skin, periosteum and adipose tissue. Human MSC, their isolation, in vitro expansion, and differentiation, have been described in, e.g., U.S. Pat. Nos. 5,486,359; 5,811,094; 5,736,396; 5,837,539; or U.S. Pat. No. 5,827,740. Any MSC described in the art and isolated by any method described in the art may be suitable in the present pharmaceutical formulations.

The term MSC also encompasses the progeny of MSC, e.g., progeny obtained by in vitro or ex vivo proliferation (propagation) of MSC obtained from a biological sample of an animal or human subject.

Preferable MSC have the potential of generating cells of at least the osteogenic (bone) lineage, such as, e.g., osteoprogenitors and/or pre-osteoblasts and/or osteoblasts and/or osteocytes, etc or of at least the chondrogenic (cartilage) lineage, such as, e.g., chondrogenic cells and/or chondroblasts and/or chondrocytes, etc.

The term "stem cell" refers generally to an unspecialized or relatively less specialized and proliferation-competent cell, which is capable of self-renewal, i.e., can proliferate without differentiation, and which or the progeny of which can give rise to at least one relatively more specialized cell type. The term encompasses stem cells capable of substantially unlimited self-renewal, i.e., wherein the progeny of a stem cell or at least part thereof substantially retains the unspecialized or relatively less specialized phenotype, the differentiation potential, and the proliferation capacity of the mother stem cell, as well as stem cells which display limited self-renewal, i.e., wherein the capacity of the progeny or part thereof for further proliferation and/or differentiation is demonstrably reduced compared to the mother cell. By means of example and not limitation, a stem cell may give rise to descendants that can differentiate along one or more lineages to produce increasingly relatively more specialized cells, wherein such descendants and/or increasingly relatively more specialized cells may themselves be stem cells as defined herein, or even to produce terminally differentiated cells, i.e., fully specialized cells, which may be post-mitotic.

The term "adult stem cell" as used herein refers to a stem cell present in or obtained from (such as isolated from) an organism at the foetal stage or after birth, such as for example after achieving adulthood.

As used herein, "osteoprogenitors" may particularly comprise early and late osteoprogenitors. "Osteoblastic cells" may particularly encompass pre-osteoblasts, osteoblasts and osteocytes, and the term may more preferably denote pre-osteoblasts and osteoblasts. All these terms are well-known per se and as used herein may typically refer to cells having an osteogenic phenotype, and that can contribute to, or are capable of developing to cells which can contribute to, the formation of bone material or bone matrix.

By means of further guidance and not limitation, osteoprogenitors and osteoblastic cells, as well as cell populations comprising osteoprogenitors and/or osteoblastic cells may display the following characteristics:

a) the cells comprise expression of Runx2, a multifunctional transcription factor that regulates osteoblast differentiation and the expression of many extracellular matrix protein genes during osteoblast differentiation;

b) the cells comprise expression of at least one of the following: alkaline phosphatase (ALP), more specifically ALP of the bone-liver-kidney type; and more preferably also comprise expression of one or more additional bone markers such as osteocalcin (OCN), procollagen type 1 amino-terminal propeptide (P1NP), osteonectin (ON), osteopontin (OP) and/or bone sialoprotein (BSP), and/or one or more additional bone matrix proteins such as decorin and/or osteoprotegerin (OPG);

c) the cells substantially do not express CD45 (e.g., less than about 10%, preferably less than about 5%, more preferably less than about 2% of the cells may express CD45);

d) the cells show evidence of ability to mineralize the external surroundings, or synthesize calcium-containing extracellular matrix (e.g., when exposed to osteogenic medium; see Jaiswal et al. J Cell Biochem, 1997, vol. 64, 295-312). Calcium accumulation inside cells and deposition into matrix proteins can be conventionally measured for example by culturing in $^{45}Ca^{2+}$, washing and re-culturing, and then determining any radioactivity present inside the cell or deposited into the extracellular matrix (U.S. Pat. No. 5,972,703), or using an Alizarin red-based mineralization assay (see, e.g., Gregory et al. Analytical Biochemistry, 2004, vol. 329, 77-84);

e) the cells substantially do not differentiate towards neither of cells of adipocytic lineage (e.g., adipocytes) or chondrocytic lineage (e.g., chondrocytes). The absence of differentiation towards such cell lineages may be tested using standard differentiation inducing conditions established in the art (e.g., see Pittenger et al. Science, 1999, vol. 284, 143-7), and assaying methods (e.g., when induced, adipocytes typically stain with oil red O showing lipid accumulation; chondrocytes typically stain with alcian blue or safranin O). Substantially lacking propensity towards adipogenic and/or chondrogenic differentiation may typically mean that less than 20%, or less than 10%, or less than 5%, or less than 1% of the tested cells would show signs of adipogenic or chondrogenic differentiation when applied to the respective test.

The cells may further comprise expression of one or more cell recruitment factors such as IL6 and/or VEGF.

As used herein, "chondroblastic cells" may particularly comprise chondroblasts, i.e., young (not matured, immature) cartilage cells active in the secretion of extracellular matrix. Chondroblasts are considered to arise by differentiation from mesenchymal stem cells. The term "chondrocyte" more specifically refers to a mature cartilage cell necessary for the maintenance of cartilaginous matrix. These terms are well-known per se and as used herein may typically refer to cells having a chondrogenic phenotype, and that can contribute to, or are capable of developing to cells which can contribute to, the formation of cartilage or cartilaginous matrix.

By means of further guidance and not limitation, human articular chondrocytes may display cell expression characteristics as summarised in Diaz-Romero et al. 2005 (J Cell Physiol, vol. 202(3), 731-42), e.g., they may express integrins and other adhesion molecules (CD49a, CD49b, CD49c, CD49e, CD49f, CD51/61, CD54, CD106, CD166, CD58, CD44), tetraspanins (CD9, CD63, CD81, CD82, CD151), receptors (CD105, CD119, CD130, CD140a, CD221, CD95, CD120a, CD71, CD14), ectoenzymes (CD10, CD26), and other surface molecules (CD90, CD99). During monolayer culture, chondrocytes may up-regulate certain markers regarded as distinctive for mesenchymal stem cells (CD10, CD90, CD105, CD166). Such markers may thus also be expressed by the less mature chondroblastic cells.

Wherein a cell is said to be positive for (or to express or comprise expression of) a particular marker, this means that a skilled person will conclude the presence or evidence of a distinct signal, e.g., antibody-detectable or detection by reverse transcription polymerase chain reaction, for that marker when carrying out the appropriate measurement, compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of the above cell-specific markers can be detected using any suitable immunological technique known in the art, such as immuno-cytochemistry or affinity adsorption, Western blot analysis, FACS, ELISA, etc., or by any suitable biochemical assay of enzyme activity (e.g., for ALP), or by any suitable technique of measuring the quantity of the marker mRNA, e.g., Northern blot, semi-quantitative or quantitative RT-PCR, etc. Sequence data for markers listed in this disclosure are known and can be obtained from public databases such as GenBank (http://www.ncbi.nlm.nih.gov/).

The present pharmaceutical formulation may comprise one or more substance with osteogenic, osteo-inductive and/or osteo-conductive properties. In preferred embodiments, such substance may be selected from the group comprising or consisting of a fibroblast growth factor (FGF), preferably FGF-2, a transforming growth factor beta (TGFB), preferably TGFB-1, platelet-derived growth factor (PDGF), interleukin-8 (IL-8), a bone morphogenetic protein (BMP), for example any one or more of BMP-2, BMP-4, BMP-6 and BMP-7, parathyroid hormone (PTH), parathyroid hormone-related protein (PTHrp), and stem cell factor (SCF). Any one such substance may be included in a pharmaceutical composition at a concentration sufficient to achieve its desired osteogenic, osteo-inductive and/or osteo-conductive effect(s) when administered to a subject, while insofar possible avoiding unwanted side effects.

Typically but without limitation, any one such substance may be comprised in the pharmaceutical formulation at a concentration between 0.01 ng/ml and 1 mg/ml, for example 0.1 ng/ml to 100 µg/ml, for example 1 ng/ml to 50 µg/ml.

The term "osteo-inductive" refers to the capacity of a component such as a peptide growth factor to recruit immature cells such as stem cells, MSC and stimulate those cells to differentiate into pre-osteoblasts and mature osteoblasts, thereby forming bone tissue. The present pharmaceutical compositions may further comprise a component with osteo-inductive properties such as an osteo-inductive protein or peptide, for instance a bone morphogenetic protein, such as BMP-2, BMP-7 or BMP-4; a hydrogel or biopolymer such as hyaluronic acid or derivatives thereof, collagen, fibrinogen, osteonectin, or osteocalcin. Preferably, the pharmaceutical compositions may further comprise hyaluronic acid or derivatives thereof, collagen or fibrinogen.

The term "osteo-conductive" refers to the ability of a component to serve as a scaffold on which bone cells can attach, migrate, grow and produce new bone. The pharmaceutical compositions may further comprise a component with osteo-conductive properties, for example, an osteo-conductive scaffold or matrix or surface such as without limitation tricalcium phosphate, hydroxyapatite, combination of hydroxyapatite/tricalcium phosphate particles (HA/TCP), gelatine, poly-lactic acid, poly-lactic glycolic acid, hyaluronic acid, chitosan, poly-L-lysine, or collagen.

As mentioned above, the pharmaceutical formulations according to the present invention may comprise components useful in the repair of bone wounds and defects. The pharmaceutical formulations may comprise a scaffold or matrix with osteo-conductive properties. The pharmaceutical formulations may be combined with demineralized bone matrix (DBM) or other matrices to make the composite osteogenic as well as osteo-conductive and osteo-inductive. Similar methods using autologous bone marrow cells with allogeneic DBM have yielded good results (Connolly et al. 1995. Clin Orthop 313: 8-18).

The pharmaceutical formulations according to the present invention may further include or be co-administered with a complementary bioactive factor or osteo-inductive protein such as a bone morphogenetic protein, such as BMP-2, BMP-7 or BMP-4, or any other growth factor. Other potential accompanying components include inorganic sources of calcium or phosphate suitable for assisting bone regeneration (WO 00/07639). If desired, cell preparation can be administered on a carrier matrix or material to provide improved tissue regeneration. For example, the material can be a hydrogel, or a biopolymer such as gelatine, collagen, hyaluronic acid or derivatives thereof, osteonectin, fibrinogen, or osteocalcin. Biomaterials can be synthesized according to standard techniques (e.g., Mikos et al., Biomaterials 14:323, 1993; Mikos et al., Polymer 35:1068, 1994; Cook et al., J. Biomed. Mater. Res. 35:513, 1997).

The formulations applying the principles of the invention advantageously display particularly good gel-forming behaviour, producing advantageously viscous formulations. In certain embodiments, the formulations are gel-forming formulations.

The terms "gel-forming", "one phase" or "monophasic" can be used interchangeably herein. The recitation "gel-forming formulation" as intended throughout this specification refers to the capacity of the formulation to form a solid, jelly-like material (gel) for instance with a pseudoplastic behaviour. For example, the present pharmaceutical formulations advantageously form a gel when its components are combined or when its components are combined with or exposed to materials and/or conditions conducive to gel formation, for example but without limitation, when dissolved or dispersed in synovial fluid, serum, or a cell composition.

The term "viscosity" generally is a measure of the resistance of a fluid which is being deformed by either shear stress or tensile stress. The present pharmaceutical formulations may have a viscosity of at least 10 Pa·s, for example the present pharmaceutical formulations may have a viscosity ranging from about 30 Pa·s to about 500 Pa·s, for example, from about 50 Pa·s to about 250 Pa·s, at room temperature when applying shear rate of 0,560 $s^{-1}$.

The compositions embodying the principles of the invention may acquire their gelatinous consistency particularly in the presence of divalent calcium ($Ca^{2+}$) ions Animal tissues, such as preferably mammalian tissues, such as more preferably human tissues, including body fluids such as synovial fluid, contain extracellular $Ca^{2+}$, typically at a concentration between 1 mM and 3 mM. Moreover, $Ca^{2+}$ concentration is high in bone tissues, where it is stored primarily as calcium phosphate crystal in the form of hydroxyapatite.

Consequently, in certain embodiments no $Ca^{2+}$ needs to be added to the present pharmaceutical compositions, since upon their administration, such as in bone or joint tissue, the $Ca^{2+}$ found at the site of administration will facilitate the coagulation/gelification of the compositions.

In certain other embodiments, $Ca^{2+}$ may be added to the present pharmaceutical compositions, for example to enhance their coagulation/gelification in situ (e.g., where $Ca^{2+}$ concentration found at the site of administration is found or expected to be inadequate to facilitate alone the coagulation/gelification of the compositions), or to achieve some degree of coagulation/gelification in vitro prior to their administration (e.g., to improve the injection capacity and/or integrity of the product). In such embodiments, $Ca^{2+}$ may be typically added in the pharmaceutical compositions at a concentration between about 5 mM and about 100 mM, preferably between about 10 mM and about 50 mM, more preferably between about 10 mM and about 20 mM, or between about 20 mM and about 40 mM, e.g., between about 20 mM and about 30 mM or between about 30 mM and about 40 mM.

In certain embodiments, products intended for intra-articular or peri-articular administration may include between about 20 mM and about 40 mM, such as between about 20 mM and about 30 mM $Ca^{2+}$. In certain other embodiments, products intended for intra-osseous or peri-osseous administration may include between about 10 mM and about 20 mM $Ca^{2+}$.

$Ca^{2+}$ may be suitably included in the pharmaceutical compositions through addition therein of a suitable amount of pharmaceutically acceptable calcium salt(s), preferably soluble calcium salt(s). Such $Ca^{2+}$ salts may be formed with inorganic or organic acids. Examples of such salts include calcium chloride ($CaCl_2$), calcium glycerophosphate, calcium phosphate, calcium hydrogen carbonate, calcium citrate, calcium sulphate, calcium lactate, calcium gluconate, calcium ascorbate, and mixtures thereof. Particularly preferred is $CaCl_2$, which displays advantageously good solubility and is well-tolerated in injectable solutions.

Pharmaceutical formulations intended herein may include between about 1 mg/ml and about 10 mg/ml $CaCl_2$, preferably between about 2 mg/ml and about 4 mg/ml of $CaCl_2$. In certain embodiments, products intended for intra-articular or peri-articular administration may include between about 1 mg/ml and about 10 mg/ml $CaCl_2$, preferably between about 2 mg/ml and about 5 mg/ml, more preferably about 4 mg/ml $CaCl_2$. In certain other embodiments, products intended for intra-osseous or peri-osseous administration may include between about 1 mg/ml and about 10 mg/ml $CaCl_2$, preferably between about 2 mg/ml and about 5 mg/ml, more preferably about 2 mg/ml $CaCl_2$.

In certain embodiments, the pharmaceutical formulations may be configured for parenteral administration, such as parenteral injection, more preferably for intra-osseous, peri-osseous, intra-articular, or peri-articular administration, such as intra-osseous, peri-osseous, intra-articular, or peri-articular injection, or for intra-tendon, peri-tendon, intra-ligament or peri-ligament administration, such as, intra-tendon, peri-tendon, intra-ligament or peri-ligament injection.

The pharmaceutical formulations or kit of parts as taught herein may be configured for local administration. The present pharmaceutical formulations or kits of parts may be configured for parenteral administration i.e., including one or more of intra-osseous, peri-osseous, intra-articular, peri-articular, intramuscular, subcutaneous, intravenous, intrasternal, intra-tendon, peri-tendon, intra-ligament or peri-ligament administration, such as including one or more of intra-osseous, peri-osseous, intra-articular, peri-articular, intramuscular, subcutaneous, intravenous, and intrasternal administration.

Preferably, the pharmaceutical formulations or kit of parts as taught herein are configured for intra-osseous or peri-osseous administration. Intra-osseous administration or delivery generally refers to a method whereby a treatment is delivered, directly or indirectly, into the bone (trabecular or cortical). Peri-osseous administration or delivery generally refers to a method whereby a treatment is delivered in the surroundings of a bone (especially around the fracture/damage site).

Particularly preferred, the pharmaceutical formulations or kit of parts as taught herein are configured for intra-articular or peri-articular administration. Intra-articular administration or delivery generally refers to a method whereby a treatment is delivered, directly or indirectly, into the synovial capsule of an articulating joint. Peri-articular administration or delivery generally refers to a method whereby a treatment is delivered in the surroundings of the synovial capsule of an articulating joint and/or the subchondral bone.

Also, the pharmaceutical formulations or kit of parts as taught herein may be configured for intra-tendon or peri-tendon administration. Also, the pharmaceutical formulations or kit of parts as taught herein may be configured for intra-ligament or peri-ligament administration.

A related aspect concerns the pharmaceutical formulation as described above for use in the treatment (including throughout the present specification therapeutic and/or preventative measures) of a musculoskeletal disease.

The term "musculoskeletal disease", as used herein, refers to any type of bone disease, muscle disease, joint disease, or chondrodystrophy, the treatment of which may benefit from the administration of the present pharmaceutical formulation to a subject having the disease. The term also encompasses diseases affecting tendons and/or ligaments). In particular, such disease may be characterized, e.g., by decreased bone and/or cartilage formation or excessive bone and/or cartilage resorption, by decreased number, viability or function of osteoblasts or osteocytes present in the bone and/or chondroblast or chondrocytes present in the cartilage, decreased bone mass and/or cartilage mass in a subject, thinning of bone, compromised bone strength or elasticity, etc.

Non-limiting examples of musculoskeletal diseases may include local or systemic disorders, such as, any type of osteoporosis or osteopenia, e.g., primary, postmenopausal, senile, corticoid-induced, bisphosphonates-induced, and radiotherapy-induced; any secondary, mono- or multisite osteonecrosis; any type of fracture, e.g., non-union, malunion, delayed union fractures or compression, conditions requiring bone fusion (e.g., spinal fusions and rebuilding), maxillo-facial fractures, congenital bone defect, bone reconstruction, e.g., after traumatic injury or cancer surgery, and cranio-facial bone reconstruction; traumatic arthritis, focal cartilage and/or joint defect, focal degenerative arthritis; osteoarthritis, degenerative arthritis, gonarthrosis, and coxarthrosis; osteogenesis imperfecta; osteolytic bone cancer; Paget's Disease, endocrinological disorders, hypophosphatemia, hypocalcemia, renal osteodystrophy, osteomalacia, adynamic bone disease, hyperparathyroidism, primary hyperparathyroidism, secondary hyperparathyroidism; periodontal disease; Gorham-Stout disease and McCune-Albright syndrome; rheumatoid arthritis; spondyloarthropathies, including ankylosing spondylitis, psoriatic arthritis, enteropathic arthropathy, and undifferentiated spondyloarthritis and reactive arthritis; systemic lupus erythematosus and related syndromes; scleroderma and related disorders; Sjogren's Syndrome; systemic vasculitis, including Giant cell arteritis (Horton's disease), Takayasu's arteritis, polymyalgia rheumatica, ANCA-associated vasculitis (such as Wegener's granulomatosis, microscopic polyangiitis, and Churg-Strauss Syndrome), Behcet's Syndrome, and other polyarteritis and related disorders (such as polyarteritis nodosa, Cogan's Syndrome, and Buerger's disease); arthritis accompanying other systemic inflammatory diseases, including amyloidosis and sarcoidosis; crystal arthropathies, including gout, calcium pyrophosphate dihydrate disease, disorders or syndromes associated with articular deposition of calcium phosphate or calcium oxalate crystals; chondrocalcinosis and neuropathic arthropathy; Felty's Syndrome and Reiter's Syndrome; Lyme disease and rheumatic fever.

The term "prophylactically effective amount" refers to an amount of an active compound or pharmaceutical active ingredient that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present formulations or pharmaceutical formulations.

In the context of the present invention a "therapeutically effective dose" means an amount of a pharmaceutical active ingredient or formulation that when administered brings about a positive therapeutic response with respect to treatment of a patient with a musculoskeletal disease such as a bone disease or a joint disease (alternatively or in addition, said disease may affect tendons and/or ligaments).

Appropriate therapeutically effective doses of a pharmaceutical active compound or pharmaceutical active ingredient in the present formulation may be determined by a qualified physician with due regard to the nature of the pharmaceutical active compound or pharmaceutical active ingredient, the disease condition and severity, and the age, size and condition of the patient.

Without limitation, a typical dose of for instance the glycosaminoglycan to be administered may range from about 2 mg to 400 mg of the glycosaminoglycan per injection. For example, the dose to be administered may range from about 4 mg to 300 mg of the glycosaminoglycan per injection, for example, from about 8 mg to 200 mg of the glycosaminoglycan per injection. Preferably, the dose to be administered ranges from about 8 mg to 160 mg of the glycosaminoglycan per injection.

Without limitation, a typical dose of for instance the cell composition to be administered may range from about $0.05 \times 10^6$ cells to $5 \times 10^9$ cells per injection. For example, the dose to be administered may range from about $0.5 \times 10^6$ cells to $1 \times 10^9$ cells per injection. Preferably, the dose to be administered ranges from about $4 \times 10^6$ cells to $250 \times 10^6$ cellsper injection.

It is recognized that the treatments of the invention may comprise administration of a single therapeutically effective dose or administration of multiple therapeutically effective doses of formulations or pharmaceutical formulations.

Except when noted, "subject" or "patient" are used interchangeably and refer to animals, preferably warm-blooded animals, more preferably vertebrates, even more preferably mammals, still more preferably primates, and specifically includes human patients and non-human mammals and primates. Preferred patients are human subjects.

As used herein, a phrase such as "a subject in need of treatment" includes subjects that would benefit from treatment of a given condition, particularly of a musculoskeletal disease such as a bone disease or a joint disease (alternatively or in addition, said disease may affect tendons and/or ligaments). Such subjects may include, without limitation, those that have been diagnosed with said condition, those prone to develop said condition and/or those in whom said condition is to be prevented.

The terms "treat" or "treatment" encompass both the therapeutic treatment of an already developed disease or condition, as well as prophylactic or preventative measures, wherein the aim is to prevent or lessen the chances of incidence of an undesired affliction, such as to prevent the chances of progression of the disease or condition. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared with expected survival if not receiving treatment.

The present pharmaceutical formulations may comprise in addition to the herein particularly specified components one or more pharmaceutically acceptable excipients. Suitable pharmaceutical excipients depend on the dosage form and identities of the active ingredients and can be selected by the skilled person (e.g. by reference to the Handbook of Pharmaceutical Excipients 6$^{th}$ Edition 2009, eds. Rowe et al.). As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active substances is well known in the art. Such materials should be non-toxic and should not interfere with the activity of the pharmaceutically active ingredients.

The precise nature of the carrier or other material will depend on the route of administration. For example, the formulation may be in the form of a parenterally acceptable aqueous solution, which is pyrogen-free and has suitable pH, isotonicity and stability.

The formulations may comprise pharmaceutically acceptable auxiliary substances as required to approximate physiological conditions, such as pH adjusting and buffering agents, preservatives, complexing agents, tonicity adjusting agents, wetting agents and the like, for example, sodium acetate, sodium lactate, sodium phosphate, sodium hydroxide, hydrogen chloride, benzyl alcohol, parabens, EDTA, sodium oleate, sodium chloride, potassium chloride, calcium chloride, sorbitan monolaurate, triethanolamine oleate, etc. Preferably, the pH value of the formulation is in the physiological pH range, such as particularly the pH of the formulation is between about 5 and about 9.5, more preferably between about 6 and about 8.5, even more preferably between about 7 and about 7.5. The preparation of such pharmaceutical formulations is within the ordinary skill of a person skilled in the art.

Another aspect relates to the use of the aforementioned formulations as a pharmaceutical excipient, more preferably as a sustained release or slow release pharmaceutical excipient.

The terms "sustained release", "slow release" or "prolonged release", as used herein, broadly refer to the release of a compound from a formulation over an extended, prolonged or increased period of time compared with the release of said compound from a reference formulation such as a formulation know in the prior art. As used herein, the sustained release refers to the prolonged release of one or more of the components of the formulations, namely of the S/D plasma, which can comprise beneficial biological substances such as endogenous growth factors, and of the glycosaminoglycan, of the cell composition, or of the one or more pharmaceutical active compounds, and optionally of one or more additional active pharmaceutical ingredient(s). For instance, it is know from the prior art that the half-life of high molecular weight hyaluronic acid in the joint is about 6 to 8 hours. The sustained release, as used herein, thus refers to the extended release of a glycosaminoglycan such as hyaluronic acid from the present formulations, for example release during one or more days, such as during 2 days, 3 days, 4 days, 5 days, 6 days, or during one or more weeks such as during 1.5 week, 2 weeks, 3 weeks, or during one or more months. These terms may thus also specifically encompass extended release, delayed release or controlled release.

EXAMPLES

Example 1

Comparison Between Human Solvent/Detergent-Treated Plasma (S/D Plasma) and Human Fresh Frozen Plasma (FFP)

Compositional Characteristics of Exemplary Formulations

The product monograph of the S/D plasma, namely Octaplas® from Octapharma AG (Lachen, Switzerland) provides a comparison between the compositional characteristics of S/D plasma and human fresh frozen plasma (FFP), as shown in Table 1. According to this information, the products have to a large extent comparable plasma protein compositions; S/D plasma may display significantly lower level of Plasmin Inhibitor.

TABLE 1

Compositional characteristics of S/D plasma, in particular Octaplas ®, and fresh frozen plasma (FFP) based on Octaplas ® product monograph

| Parameter | S/D plasma (n = 12) Mean (min-max) | Reference ranges FFP |
|---|---|---|
| Total protein (mg/mL) | 55 (54-57) | 48-64 |
| Albumin (mg/mL) | 2 (30-34) | 28-41 |
| Fibrinogen (mg/mL) | 2.5 (2.4-2.6) | 1.45-3.85 |
| IgG (mg/mL) | 9.65 (9.15-10.10) | 6.60-14.50 |
| IgA (mg/mL) | 2.00 (1.80-2.05) | 0.75-4.20 |
| IgM (mg/mL) | 1.25 (1.20-1.30) | 0.40-3.10 |
| Factor V (IU/mL) | 0.78 (0.75-0.74) | 0.54-1.45 |
| Factor VII (IU/mL) | 1.08 (0.90-1.17) | 0.62-1.65 |
| Factor X (IU/mL) | 0.78 (0.75-0.80) | 0.68-1.48 |
| Factor XI (IU/mL) | 0.99 (0.91-1.04) | 0.42-1.44 |
| Protein C (IU/mL) | 0.85 (0.81-0.87) | 0.58-1.64 |
| Protein S (IU/mL) | 0.64 (0.55-0.71) | 0.56-1.68 |
| Plasmin inhibitor (IU/ml) | 0.23 (0.20-0.27) | 0.72-1.32 |

Reviewing the composition of S/D plasma, in particular Octaplas®, and fresh frozen plasma, Svae et al. 2007 concluded that there were no critical reductions in the activities of coagulation factors and naturally occurring inhibitors caused by the manufacturing process, including S/D treatment, while Protein S and Plasmin Inhibitor could show a 35% and 76% decrease, respectively (Beeck & Hellstern 1998). Doyle et al. 2003 reported significantly lower levels of Protein S (38%), Plasmin Inhibitor (78%), as well as Factor XI (13%) and Factor V (13%), and significantly increased levels of Factor VII (15%) in S/D plasma by comparing 16 Octaplas® batches with 48 unpaired FFP units.

Reference is made to Table 1 of Svae et al. 2007 presenting the compositional characteristics of 12 consecutive batches of Octaplas® vs. 12 random units of quarantined FFP. While most components were not significantly altered, the following Table 2 reproduces those components of Table 1 of Svae et al. 2007 which showed significant differences (P value <0.05, unpaired t-test).

TABLE 2

Compositional differences between S/D plasma, namely Octaplas ®, and FFP, based on Table 1 of Svae et al. 2007

| Parameter | Normal range | Octaplas ® | quarantined FFP | P value |
|---|---|---|---|---|
| Fibrinogen (mg 100 mL$^{-1}$) | 145-385 | 249 (246-253) | 257 (231-283) | <0.05 |
| Factor VII (IU 100 mL$^{-1}$) | 62-165 | 108 (105-112) | 95 (84-105) | <0.05 |
| Factor XI (IU 100 mL$^{-1}$) | 42-144 | 99 (97-101) | 113 (101-125) | <0.05 |
| Protein S activity (IU 100 mL$^{-1}$) | 56-168 | 64 (61-66) | 103 (93-112) | <0.001 |
| Plasmin Inhibitor (IU 100 mL$^{-1}$) | 72-132 | 23 (22-25) | 104 (101-107) | <0.001 |

Also, Theusinger et al. 2011 (Br. J. Anaesth., 106(4):505-11) studied the relative concentrations of haemostatic factors and cytokines in S/D plasma, namely Octaplas®, and fresh frozen plasma (n=25). They observed that coagulation factor content was similar for S/D plasma and FFP, but S/D plasma contained less Factor V, von Willebrand factor (vWF), and von Willebrand factor-cleaving protease (vWFCP, ADAMTS-13). Cytokine concentrations (TNFα, IL-8, and IL-10) were significantly higher in FFP.

Moreover, S/D process may lead to losses of the labile Factor V, Factor VIII, the serine protease inhibitor (serpin) activities of α1-antitrypsin and α2-antiplasmin, but not antithrombin (Benjamin & McLaughtin 2012; Mast et al. 1999). Factor VIII loss is associated with a decrease in high molecular weight von Willebrand Factor (vWF). In a study of Sachs et al. 2005 S/D plasma samples (n=5) tested negative for granulocyte-specific as well as HLA Class I and Class II antibodies.

Table 3 provides an overview of demonstrable distinctions between S/D plasma, namely Octaplas®, and fresh frozen plasma, as detected in the aforementioned studies.

TABLE 3

Exemplary differences between S/D plasma, namely Octaplas ®, and fresh frozen plasma

| Parameter | Octaplas ® | FFP | References |
|---|---|---|---|
| Protein S activity | Reduced | Normal | Octapharma AG website Doyle et al. 2003 Benjamin & McLaughtin 2012 |
| Factor V* | Reduced | Normal | Doyle et al. 2003 Theusinger et al. 2011 Benjamin & McLaughtin 2012 |
| Factor VIII* | Reduced | Normal | Doyle et al. 2003 |
| Factor X | Reduced | Normal | Benjamin & McLaughtin 2012 |
| α2-antiplasmin | Reduced | Normal | Benjamin & McLaughtin 2012 |
| Antitrypsin | Reduced | Normal | Mast et al. 1999 |
| vWF | Reduced | Normal | Theusinger et al. 2011 |
| ADAMTS-13 | Reduced | Normal | Theusinger et al. 2011 |
| Cytokines (TNFα, IL-8, IL-10) | Reduced | Normal | Theusinger et al. 2011 |
| Presence of solvent, detergent | TNBP 2 µg/ml (max) Triton X-100 5 µg/ml (max) | — | Octapharma AG website |
| Excipient | Sodium citrate dihydrate Sodium dihydrogenphosphate dihydrate Glycine | — | Octapharma AG website |

In conclusion, numerous compositional differences have been documented between human S/D plasma and fresh frozen plasma. Particularly marked characteristic of S/D plasma may be a reduced level of Plasmin Inhibitor vs. FFP, such as Plasmin Inhibitor level equal to or less than 0.60 IU/ml or equal to or less than 0.50 IU/ml, for example Plasmin Inhibitor level between 0.20 and 0.30 IU/ml, more specifically between 0.22 and 0.25 IU/ml.

Coagulation Behaviour

The ensuing experiments employed the following human plasma types: S/D plasma, namely Octaplas®, plasma processed in a heparinised tube, plasma processed in a tube containing EDTA, or plasma processed in citrated tube. The plasma was prepared as follows: blood was directly collected in corresponding tubes, i.e., heparinated, EDTA, or citrated tubes and the tubes were centrifuged at 1500 g for 10 minutes at room temperature to collect the plasma as supernatant. Because S/D plasma is plasma decellularised by filtration, the other plasma types were, where so denoted, filtered through a 0.2 μm filter to ensure the absence of cells, such as platelets, or debris. The volume of the mixture reaction was 250 μl or 500 μl. Each constituent and the mixture were maintained at 37° C. The coagulation time was determined at 37° C. for a mixture containing the respective plasma type, 10 or 20% v/v of serum, and 2.5 or 5% v/v $CaCl_2$ (0.546 M) The clotting time was measured by visual observation optionally during or after agitation of the tube. Five samples were tested. Results are summarized in Table 4.

There was no distinction in the results obtained for 2.5% and 5% $CaCl_2$ and for 10 or 20% serum.

TABLE 4

Coagulation behaviour of S/D plasma, namely Octaplas ®, versus other plasma types

| Plasma | Unfiltered (n = 5) | | Filtered (n = 5) | |
| --- | --- | --- | --- | --- |
| | Mean coagulation time (sec) | SD | Mean coagulation time (sec) | SD |
| S/D plasma | 588 | 62 | 594 | 91 |
| Heparinised | ND (>1 h) | / | ND (>1 h) | / |
| EDTA | 804 | 465 | 1320 | 659 |
| Citrated | 384 | 271 | 816 | 343 |

Clot formation was not observed with heparinised plasma, either unfiltered or filtered (decellularised). Filtration of S/D plasma displayed no significant differences in coagulation time (p=0.7780, Paired t Test) while a significant increase is observed for EDTA plasma (p=0.0053, Paired t Test) and for citrated plasma (p=0.0143, Paired t Test). However, clot formation with S/D plasma was about 50% to over 100% faster compared with citrated plasma and EDTA plasma, respectively. Consequently, S/D plasma, exemplified by Octaplas®, differs from other plasma types with respect to coagulation properties.

A marked characteristic of S/D plasma, particularly decellularised S/D plasma, may therefore be a reduced coagulation time. For example, the coagulation time may be less than or equal to 700 sec, or less than or equal to 600 sec, such as between 500 and 700 sec, or between 550 and 600 sec, when measured at 37° C. in a mixture comprising human decellularised S/D plasma, 10 or 20% v/v of serum and 2.5 or 5% w/v $CaCl_2$ (0.546 M).

Example 2

Gel Formation by Human Solvent/Detergent (S/D)-Treated Plasma (Octaplas®) and Hyaluronic Acid (HA)

Clot/Gel Formation by Octaplas® and HA

The behaviour of human S/D plasma, in particular Octaplas®, was tested in combination with synovial fluid from arthritic patients (n=2). The synovial fluid was contacted at a ratio 1:1 v/v with a formulation according to an embodiment of the present invention comprising Octaplas®, hyaluronic acid (10 mg/ml sodium hyaluronate, molecular weight of $1.8\text{-}2.10^6$ Da, provided by Contipro, Czech Republic) and $CaCl_2$. Three concentrations of $CaCl_2$, i.e. 0, 2 and 4 mg/ml $CaCl_2$, were tested. The gel formation was evaluated visually after different time-points (20-30 min, 1 h, 2 h) using a timer. Viscosity was evaluated by measuring the time needed for the solutions to reach a defined scale on the container wall when the reaction tube was turned upside down. The test was performed twice on synovial fluid from two arthritic patients.

Incubation of a formulation including 4 mg/ml $CaCl_2$ with synovial fluid induced the formation of a gel which was more viscous compared with a gel obtained by contacting synovial fluid with a formulation including 2 mg/ml $CaCl_2$. Upon contacting a formulation without $CaCl_2$ with synovial fluid, no clot formation was observed.

Clot/Gel Formation by OctaplasLG AB® and HA in the Presence of Synovial Fluid

The behaviour of human S/D plasma, in particular OctaplasLG AB®, was tested in combination with synovial fluid from osteoarthritic patients (n=5). The synovial fluid of these patients was mixed at a ratio 1:2 (v/v) with a formulation according to an embodiment of the present invention comprising OctaplasLG AB®, HA (10 mg/ml sodium hyaluronate, molecular weight of $2\text{-}3.10^6$ Da, provided by HTL Biotechnology, France), clonidine hydrochloride (HCl) (200 m/ml, purchased from PCAS laboratory, Finland) and $CaCl_2$ (4 mg/ml Calciclo®, provided by Sterop Group, Belgium) to mimic the clinical condition. Clot/gel formation was evaluated visually after 30 minutes at 37° C. (humidified incubator, 5% $CO_2$).

Once in contact with synovial fluid, this formulation formed a clot in 30 minutes.

In another experiment, three concentrations of $CaCl_2$ (i.e., 0, 2 and 4 mg/ml $CaCl_2$) were tested in the above mentioned formulation. The test was performed twice on synovial fluid from osteoarthritic patients (n=2). Incubation of a formulation including 4 mg/ml or 2 mg/ml $CaCl_2$ with synovial fluid induced the formation of a gel of the same viscosity. However, upon mixing a formulation without $CaCl_2$ with synovial fluid, no clot formation was observed. The dose of 2 mg/ml of $CaCl_2$ (14 mM) was thus chosen in the final formulation.

In conclusion, in this experiment $Ca^{2+}$ was required for clot formation in the presence of synovial fluid. $Ca^{2+}$ may need to be added to a formulation illustrating the present invention in particular when it is found or expected not to be present at adequate levels in joint tissues.

Clot/Gel Formation by OctaplasLG AB® and HA in the Presence of Whole Blood

The gelifying effect of OctaplasLG AB® with HA in combination with whole blood from a healthy donor (n=1) was investigated in order to evaluate its potential to form a matrix including platelet-derived growth factors. In this study, the behaviour of a formulation comprising OctaplasLG AB®, HA (4 mg/ml sodium hyaluronate, molecular weight of 2-3.10$^6$ Da, provided by HTL Biotechnology, France) and CaCl$_2$ (2 mg/ml Calciclo®, provided by Sterop Group, Belgium) was tested in combination with whole blood collected in citrated tubes (#VF054SBCS07, Venosafe, Terumo). The clotting time was measured by visual observation after tube agitation/solution homogenisation.

Results showed that once in contact with citrated blood at a ratio 1:1 (v/v), this formulation formed a clot in 15 minutes at 37° C. (humidified incubator, 5% CO$_2$).

Clot/Gel Formation by Octaplas® and HA Compared to Other Plasma Types

The consistence of several formulations was tested. The formulations contained hyaluronic acid (Sodium hyaluronate, molecular weight of 2-3.10$^6$ Da, provided by HTL, France), CaCl$_2$ and Octaplas® or the same volume of the following human plasma types (unfiltered): plasma processed in a heparinised tube, plasma processed in a tube containing EDTA, or plasma processed in citrated tube (see Table 5 for the composition of the formulations).

TABLE 5

Composition of the formulations

|  | Volume | Stock solution | Final concentration |
|---|---|---|---|
| Plasma | 950 or 900 µl | 100% | 95 or 90% |
| CaCl$_2$ | 50 or 100 µl | 80.3 mg/ml | 4 or 8 mg/ml |
| hyaluronic acid | NA | NA | 4 to 20 mg/ml |

Human serum prepared from peripheral blood at a ratio 1:1 v/v was added to the product and incubated at 37° C. with agitation. The consistence was observed visually after 30 minutes, 1 h and 24 h.

Table 6 provides a semi-quantitative assessment of gelification with the various plasma types. After 1 hour, the formulation containing Octaplas® displayed a viscous consistence, even gelified consistence. The formulation containing heparinised plasma remained liquid after 1 hour (Table 6). The formulation containing Octaplas® was more viscous than formulations containing plasma processed in a tube containing EDTA or plasma processed in citrated tube (Table 6). Consequently, the formulation containing Octaplas® was more viscous than formulations containing the other plasma types.

TABLE 6

Gelification with Octaplas ® vs. other plasma types (unfiltered) in the presence of HA

| Plasma | Consistence after 30 min | Consistence after 1 h | Consistence after 24 h |
|---|---|---|---|
| Octaplas ® | Viscous+++ | Viscous++++ | Viscous++ |
| Heparinised plasma | Liquid | Liquid | Liquid |
| EDTA plasma | Viscous+ | Viscous+ | ND |
| Citrated plasma** | Viscous+ | Viscous+ | ND |

*Octaplas ® is filtered plasma, i.e., plasma without cellular constituents/components.
**Results obtained after agitation Clot/Gel Formation by Octaplas® in the Presence or Absence of HA Consistency was compared between formulations containing Octaplas®, CaCl$_2$ and serum, with or without hyaluronic acid (Sodium hyaluronate, molecular weight of 2-3.10$^6$ Da, provided by HTL, France). A formulation without hyaluronic acid was prepared at 37° C. by mixing the following components: 2 ml of Octaplas®, 222 µl of serum, and 22 µl of 30 mg/ml CaCl$_2$ stock solution (prepared from CaCl$_2$ salt of Sigma in water). A formulation with hyaluronic acid was prepared at 37° C. by mixing the following components: 8 mg HA previously dissolved in 2 ml of Octaplas®, 222 µl of serum, and 22 µl of 30 mg/ml CaCl$_2$stock solution (prepared from CaCl$_2$ salt from Sigma in water). The clotting time was measured by visual observation and agitation of the tube. The test was performed once.

Upon visual inspection, a clot or gelified phase was formed in both formulations. The formulation with HA however contained noticeably less liquid phase and could be manipulated without change. On the contrary, the clot without HA broke and released liquid upon manipulation of the clot.

Cell Delivery Formulation Based on S/D Plasma and HA

An exemplary, non-limiting formulation suitable for intra-osseous delivery of cells to a human subject comprises, consists essentially of or consists of human S/D plasma, particularly Octaplas®, 20 mg/ml HA, a cell composition comprising autologous or allogeneic mesenchymal stem cells (MSC) isolated from human bone marrow or a cell composition comprising osteoblastic cells, and 20 mg/ml CaCl$_2$. The formulation is administered to a bone defect site in the patient.

Example 3

Gel Formation by Human S/D Plasma Such as Octaplas® and a Cell Composition

Clot/Gel Formation by Octaplas® and Ca$^{2+}$-Containing Cell Culture Medium

Clot formation was tested for several formulations without cells but comprising human S/D plasma, in particular Octaplas®, a conventional culture medium (which contains CaCl$_2$) and human serum. Different conditions were tested to verify clot formation at 37° C. such as Octaplas® at different concentrations, e.g., 5%, v/v 7.5% v/v, or 10% v/v; different conventional culture media, e.g., DMEM, MEM, PBS, or PBS plus CaCl$_2$; and the absence or presence of 5 or 10% v/v serum. Formation of a clot was visually observed when Octaplas®, a conventional culture medium (which contains CaCl$_2$) and serum were combined in the absence of cells.

It could be concluded that presence of serum as well as presence of calcium in the culture medium appeared necessary for clot formation in the absence of cells.

Clot/Gel Formation by Octaplas® and a Cell Composition

Bone marrow MSC were plated at 57000 cells/cm$^2$ in plastic flasks in conventional culture medium (DMEM) containing 5% v/v, 10% v/v, or 15% v/v S/D plasma, in particular Octaplas®. Flasks were directly placed at 37° C. in a 5% CO$_2$ incubator. Gelification of the medium was observed in less than one hour at 37° C. Cell medium containing human S/D plasma, in particular Octaplas®, changed consistency from liquid to gelified (gel) in 30 minutes after contact.

The above data show the ability of a formulation comprising S/D plasma and cells in Ca$^{2+}$-containing cell culture medium to gelify in comparison with a cell culture in Ca$^{2+}$-containing cell culture medium with serum, i.e., in conventional cell culture conditions, of which it is generally know that these stay liquid.

Clot/Gel Formation by Octaplas®, Other Plasma Types, and a Cell Composition

The consistency of a cell culture composition with different types of human plasma—Octaplas®, plasma processed in a heparinised tube, plasma processed in a tube containing EDTA, or plasma processed in citrated tube—was assessed.

57000 cells/cm$^2$ osteoprogenitor cells cultured from bone marrow cells were seeded in plastic T25 flask in 6 ml culture medium (85% v/v) supplemented with 15% v/v of the respective plasma at 37° C. Results are summarized in Table 7. The medium remained liquid with heparinised plasma (Table 7). No difference was observed in this initial experiment between Octaplas®, EDTA-plasma and citrated plasma (Table 7).

TABLE 7

Gelification/coagulation time for the different tested plasma types in the presence of cells

| Plasma (unfiltered) | Time of gelification** |
|---|---|
| Octaplas ®* | <15 min |
| Heparinised plasma | >1 h (no gelification) |
| EDTA plasma | <15 min |
| Citrated plasma | <15 min |

*Octaplas is filtered plasma, i.e., plasma without cellular constituents/components.
**Three cell cultures were tested for each plasma type Cell Delivery Formulation Based on S/D Plasma An exemplary, non-limiting formulation suitable for intraosseous delivery of cells to a mammalian subject comprises, consists essentially of or consists of S/D plasma, particularly Octaplas®, a cell composition comprising autologous or allogeneic mesenchymal stem cells (MSC) isolated from bone marrow or a cell composition comprising osteoblastic cells, and 2-8 mg/ml CaCl$_2$. The formulation is administered to a bone defect site in a mice model of calvaria osteotomy.

Example 4

Gel Formation by Human S/D Plasma Such as Octaplas®

An exemplary, non-limiting pharmaceutical formulation comprising S/D plasma and a pharmaceutical active ingredient, wherein the formulation is suitable for therapeutic use in bone defects, consists essentially of or consists of S/D plasma, particularly Octaplas®, a growth factor (IL-8 at 30 µg/ml) and 2-8 mg/ml CaCl$_2$. The formulation is administered to a bone defect site in a nude mouse model of calvaria osteotomy. 4 weeks after the administration of the formulation, bone repair can be clearly seen in the treated mice compared to control without IL-8 (see FIGS. 1 and 2).

CITATION LIST

Non Patent Literature

Beeck H, Hellstern P. In vitro characterization of solvent/detergent-treated human plasma and of quarantine fresh frozen plasma. Vox Sang. 1998; 74 Suppl 1:219-23.
Benjamin R J, McLaughlin L S. Plasma components: properties, differences, and uses. Transfusion. 2012 May; 52 Suppl 1:9S-19S.
Burgess W H, Maciag T. The heparin-binding (fibroblast) growth factor family of proteins. Annu Rev Biochem. 1989; 58:575-606.
Cole, B. J., Seroyer, S. T., Filardo, G., Bajaj, S., Fortier, L. A., 2010. Platelet-Rich Plasma. Sports Health 2, 203-210.
Doyle S, O'Brien P, Murphy K, Fleming C, O'Donnell J. Coagulation factor content of solvent/detergent plasma compared with fresh frozen plasma. Blood Coagul Fibrinolysis. 2003 April; 14(3):283-7.
Frescaline G, Bouderlique T, Huynh M B, Papy-Garcia D, Courty J, Albanese P. Glycosaminoglycans mimetics potentiate the clonogenicity, proliferation, migration and differentiation properties of rat mesenchymal stem cells. Stem Cell Res. 2012 March; 8(2):180-92.
Gobbi, A., Bathan, L., 2009. Biological approaches for cartilage repair. J Knee Surg 22, 36-44.
Grimaud, E., Heymann, D., Rédini, F., 2002. Recent advances in TGF-beta effects on chondrocyte metabolism. Potential therapeutic roles of TGF-beta in cartilage disorders. Cytokine Growth Factor Rev. 13, 241-257.
Hausser H J, Brenner R E. Low doses and high doses of heparin have different effects on osteoblast-like Saos-2 cells in vitro. J Cell Biochem. 2004 Apr. 1; 91(5):1062-73.
Hellstern P, Solheim B G. The Use of Solvent/Detergent Treatment in Pathogen Reduction of Plasma. Transfus Med Hemother. 2011; 38(1):65-70.
Horowitz B, Bonomo R, Prince A M, Chin S N, Brotman B, Shulman R W. Solvent/detergent-treated plasma: a virus-inactivated substitute for fresh frozen plasma. Blood. 1992 Feb. 1; 79(3):826-31.
Lyon M, Rushton G, Gallagher J T. The interaction of the transforming growth factor-betas with heparin/heparan sulfate is isoform-specific. J Biol Chem. 1997 Jul. 18; 272(29):18000-6.
Mast A E, Stadanlick J E, Lockett J M, Dietzen D J. Solvent/detergent-treated plasma has decreased antitrypsin activity and absent antiplasmin activity. Blood. 1999 Dec. 1; 94(11):3922-7.
McCaffrey T A, Falcone D J, Brayton C F, Agarwal L A, Welt F G, Weksler B B. Transforming growth factor-beta activity is potentiated by heparin via dissociation of the transforming growth factor-beta/alpha 2-macroglobulin inactive complex. J Cell Biol. 1989 July; 109(1):441-8.
Park S H, Cui J H, Park S R, Min B H. Potential of fortified fibrin/hyaluronic acid composite gel as a cell delivery vehicle for chondrocytes. Artif Organs. 2009 June; 33(6): 439-47.
Sachs U J, Kauschat D, Bein G. White blood cell-reactive antibodies are undetectable in solvent/detergent plasma. Transfusion. 2005 October; 45(10):1628-31.
Svae T E, Frenzel W, Heger A, Romisch J. Quality differences between solvent/detergent plasmas and fresh-frozen plasma. Transfus Med. 2007 August; 17(4):318-20.

The invention claimed is:

1. A pharmaceutical formulation comprising solvent/detergent treated plasma (S/D plasma) and hyaluronic acid or a derivative thereof, wherein the hyaluronic acid or derivative thereof is in a concentration ranging from about 1 mg/ml to about 20 mg/ml.

2. The pharmaceutical formulation according to claim 1, wherein the pharmaceutical formulation is produced by combining the S/D plasma and the hyaluronic acid or derivative thereof.

3. The pharmaceutical formulation according to claim 1, wherein the S/D plasma is human S/D plasma.

4. The pharmaceutical formulation according to claim 1, further comprising one or more pharmaceutically active ingredients.

5. The pharmaceutical formulation according to claim 4, wherein the one or more pharmaceutically active ingredients is selected from the group consisting of a cell composition, a pharmaceutically active compound, a protein, a peptide, and a small organic molecule, and wherein the cell composition comprises mesenchymal stem cells (MSC), osteoprogenitors, osteoblastic cells, osteocytes, chondroblastic cells, and chondrocytes.

6. The pharmaceutical formulation according to claim 5, wherein the pharmaceutically active compound is an alpha-2 adrenergic receptor agonist selected from the group consisting of clonidine and derivatives thereof.

7. The pharmaceutical formulation according to claim 5, wherein the pharmaceutically active protein or peptide is a growth factor selected from the group consisting of a fibroblast growth factor (FGF), a transforming growth factor beta (TGFB), platelet-derived growth factor (PDGF), interleukin-8 (IL-8), a bone morphogenetic protein (BMP), parathyroid hormone (PTH), parathyroid hormone-related protein (PTHrp), and stem cell factor (SCF).

8. The pharmaceutical formulation according to claim 1, further comprising a proteoglycan or derivative thereof, a chondroitin sulfate, a keratin sulfate, a chitosan or derivative thereof, a chitin or derivative thereof, or a mixture thereof.

9. The pharmaceutical formulation according to claim 1, further comprising human serum.

10. The pharmaceutical formulation according to claim 1, wherein the pharmaceutical formulation is configured for parenteral administration.

11. The pharmaceutical formulation according to claim 10, wherein the parental administration is intra-osseous, peri-osseous administration, intra-articular administration, peri-articular administration, intra-tendon administration, peri-tendon administration, intra-ligament administration, or peri-ligament administration.

12. The pharmaceutical formulation according to claim 1 for use in the treatment of a musculoskeletal disease, wherein the musculoskeletal disease is a bone disease or a joint disease.

13. A method of treating osteoarthritis in a subject in need thereof comprising administering to the subject a therapeutically or prophylactically effective amount of the pharmaceutical formulation of claim 1, wherein the pharmaceutical formulation is administered by intra-articular administration.

14. The method according to claim 13, wherein the pharmaceutical formulation is produced by combining the S/D plasma and the hyaluronic acid or derivative thereof.

15. The method according to claim 13, wherein the S/D plasma is human S/D plasma.

* * * * *